US007163787B2

(12) United States Patent
Brus et al.

(10) Patent No.: US 7,163,787 B2
(45) Date of Patent: Jan. 16, 2007

(54) METHODS FOR THE IDENTIFICATION OF ANTIVIRAL COMPOUNDS

(75) Inventors: Ronald H. P. Brus, Voorschoten (NL); Govert Johan Schouten, Leiderdorp (NL); Alphonsus G. C. M. UytdeHaag, Utrecht (NL)

(73) Assignee: Crucell Holland B.V., Leiden (NL)

( * ) Notice: Subject to any disclaimer, the term of this patent is extended or adjusted under 35 U.S.C. 154(b) by 0 days.

(21) Appl. No.: 10/698,086

(22) Filed: Oct. 30, 2003

(65) Prior Publication Data

US 2004/0086850 A1 May 6, 2004

Related U.S. Application Data

(63) Continuation of application No. PCT/NL02/00296, filed on May 6, 2002.

(60) Provisional application No. 60/289,541, filed on May 7, 2002.

(30) Foreign Application Priority Data

May 7, 2001 (EP) ................................. 01201657

(51) Int. Cl.
*C12Q 1/00* (2006.01)
*C12Q 1/02* (2006.01)
*C12Q 1/18* (2006.01)
*C12Q 1/70* (2006.01)
*C12N 5/00* (2006.01)
*C12N 5/08* (2006.01)
*C12N 5/10* (2006.01)

(52) U.S. Cl. .................... 435/5; 435/4; 435/29; 435/32; 435/325; 435/366

(58) Field of Classification Search ............... 435/4, 435/5, 6, 7.2, 7.21, 7.23, 29, 32, 91.33, 235.1, 435/238, 325, 366, 320.1; 536/23.72
See application file for complete search history.

(56) References Cited

U.S. PATENT DOCUMENTS

| 5,994,128 | A | * | 11/1999 | Fallaux et al. ............... 435/325 |
| 6,033,908 | A | | 3/2000 | Bout et al. |
| 6,071,744 | A | * | 6/2000 | Scholl et al. ................ 435/325 |
| 6,200,745 | B1 | | 3/2001 | Kreider et al. |
| 6,218,105 | B1 | | 4/2001 | Hall et al. |
| 2002/0076789 | A1 | * | 6/2002 | Homa et al. ................. 435/199 |
| 2006/0051747 | A1 | * | 3/2006 | Pau et al. ..................... 435/5 |
| 2006/0063261 | A1 | * | 3/2006 | Pau et al. ................... 435/456 |

FOREIGN PATENT DOCUMENTS

| EP | 0978566 A2 | 2/2000 |
| WO | WO 91/15573 | 10/1991 |
| WO | WO 97/00326 | 1/1997 |
| WO | WO 99/51776 | 10/1999 |
| WO | WO 99/64582 | 12/1999 |
| WO | WO 00/63403 | 10/2000 |
| WO | WO 01/38362 | 5/2001 |
| WO | WO 02/090982 A1 | 11/2002 |

OTHER PUBLICATIONS

Lin et al., Journal of Virological Methods, vol. 88 No. 2, pp. 219-225 (Aug. 2000).*
Spector et al., Journal of Virology, vol. 72 No. 9, pp. 6979-6987 (Sep. 1998).*
Cotarelo et al., Journal of Antimicrobial Chemotherapy, vol. 44 No. 5, pp. 705-708 (Nov. 1999).*
PCT International Search Report, PCT/NL02/00296, dated Oct. 7, 2002.
PCT International Preliminary Examination Report, PCT/NL02/00296, dated Mar. 13, 2003, 2 pages.
PCT Written Opinion, PCT/NL02/00296, Dec. 19, 2002.
Gallimore et al., Transformation of Human Embryo Retinoblasts with Simian Virus 40, Adenovirus and ras Oncogenes, Anticancer Research, 1986, pp. 499-508, vol. 6.
Lewin, Benjamin, Genes V, 1994, p. 1184, Oxford University Press and Cell Press.

* cited by examiner

*Primary Examiner*—Bruce R. Campell
*Assistant Examiner*—Zachariah Lucas
(74) *Attorney, Agent, or Firm*—TraskBritt

(57) ABSTRACT

The present invention provides novel methods for determining whether a compound influences a phase in the life cycle of a virus comprising providing a cell with the compound and with at least a fragment of the virus sufficient for performing the phase and determining whether the phase is influenced in the cell, the cell comprising a nucleic acid encoding an adenovirus early protein or a functional part, derivative and/or analogue of the adenovirus early protein. In another aspect, the invention provides the use of a cell, the cell comprising nucleic acid encoding an adenovirus early protein, for screening a library of compounds for the presence of a compound capable of influencing a phase in the life cycle of a virus capable of entering the cell. The invention also provides novel methods for identifying a compound with antiviral activity comprising providing a cell with at least a fragment of a virus, the fragment capable of performing a step in the life cycle of the virus, providing the cell with a compound and determining whether the compound is capable of influencing the step in the life cycle of the virus, wherein the cell comprises a nucleic acid encoding an adenovirus early protein or a functional part, derivative and/or analogue of the adenovirus early protein.

7 Claims, 25 Drawing Sheets

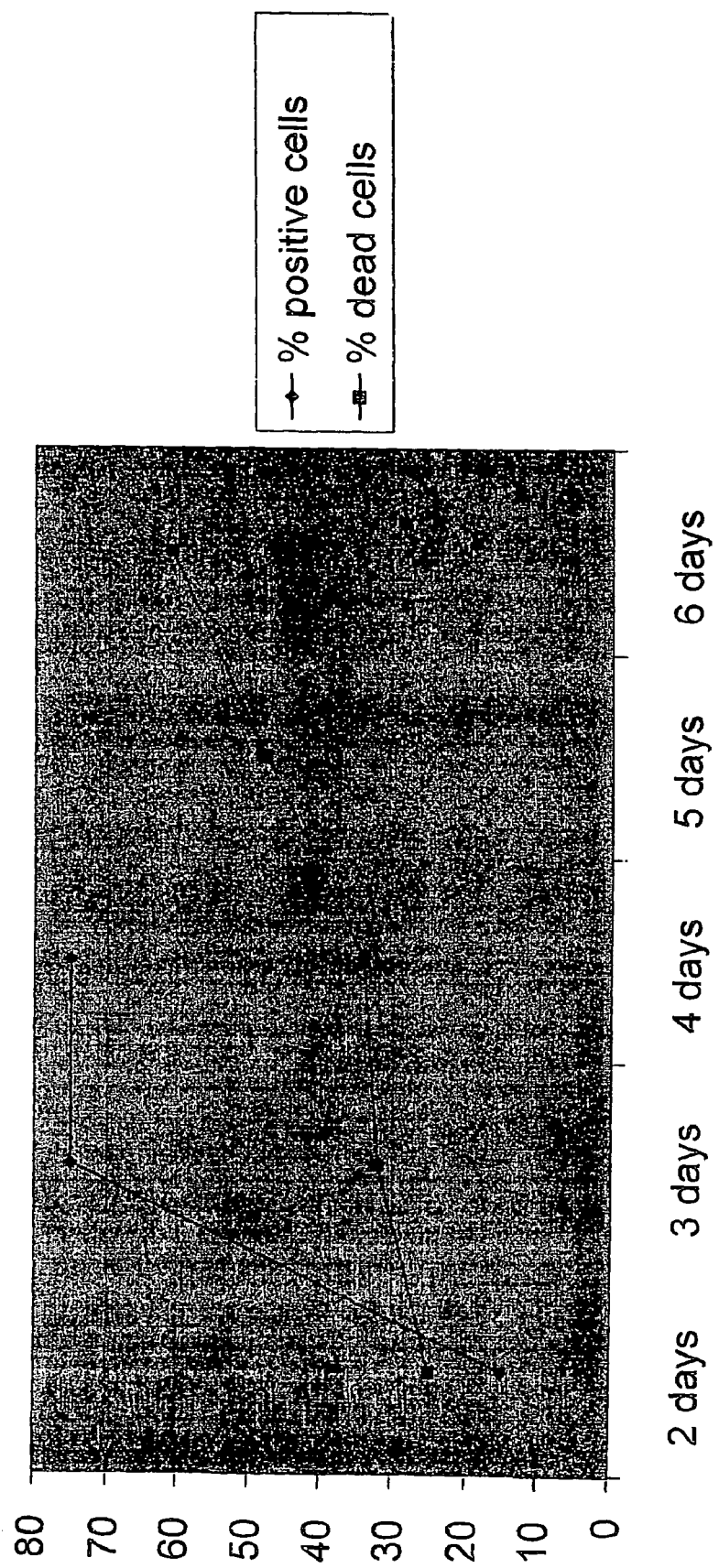

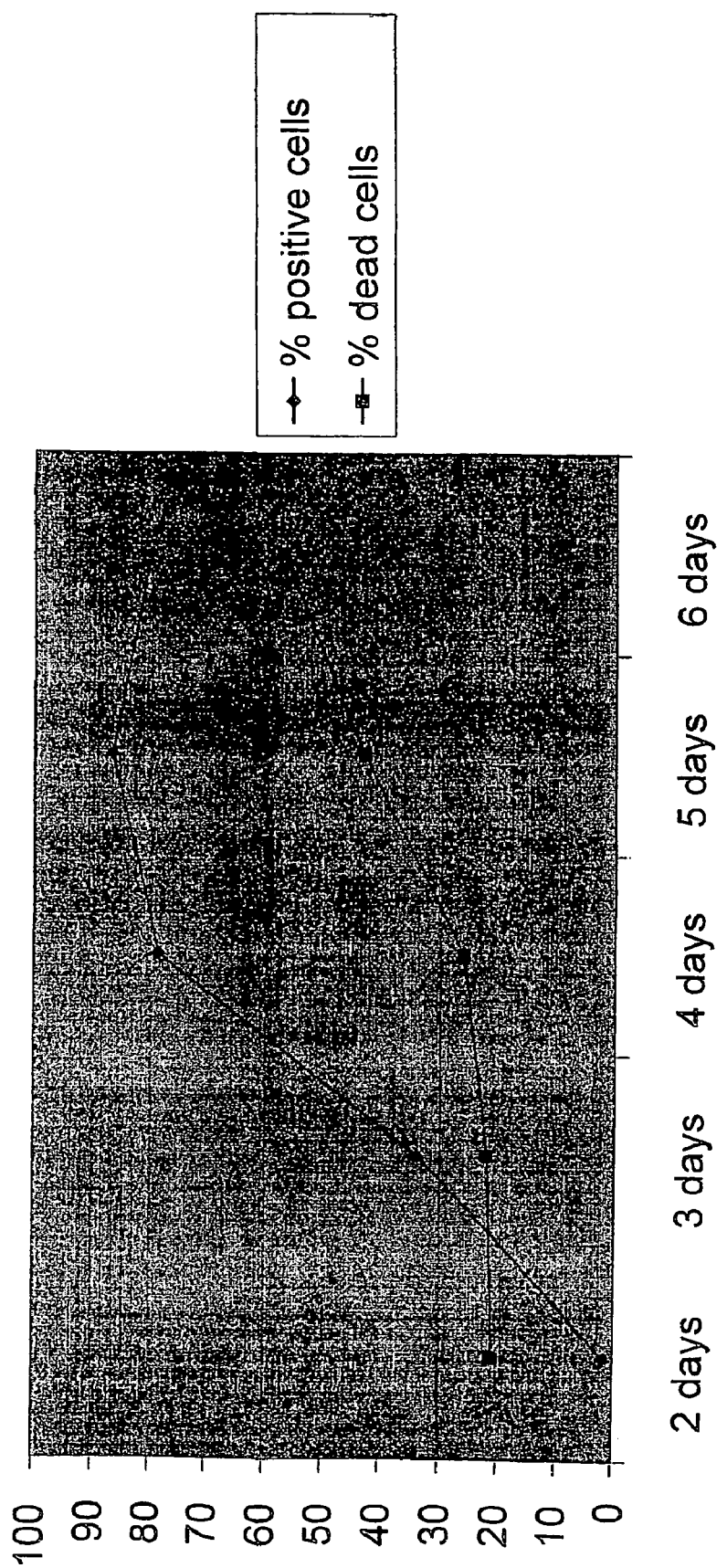

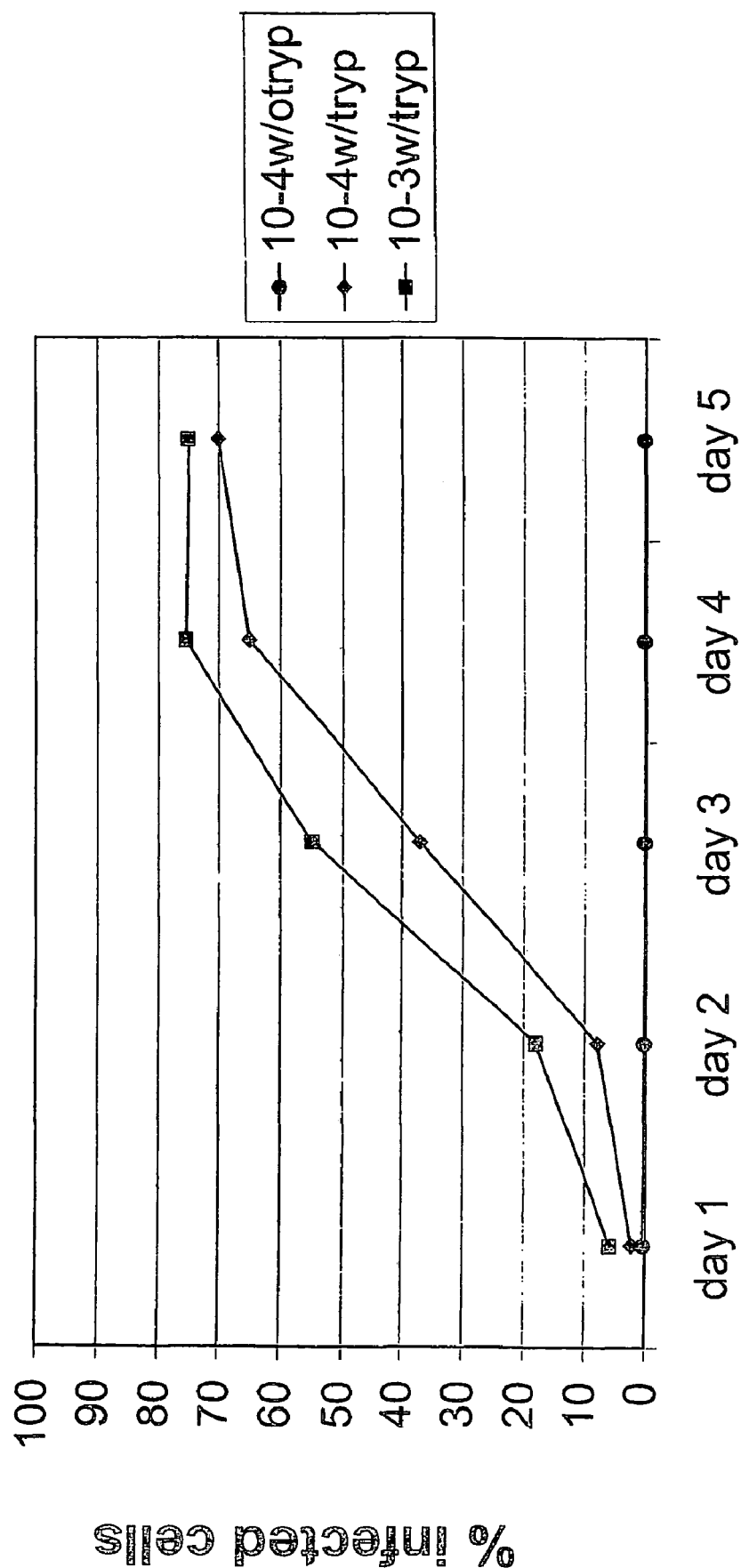

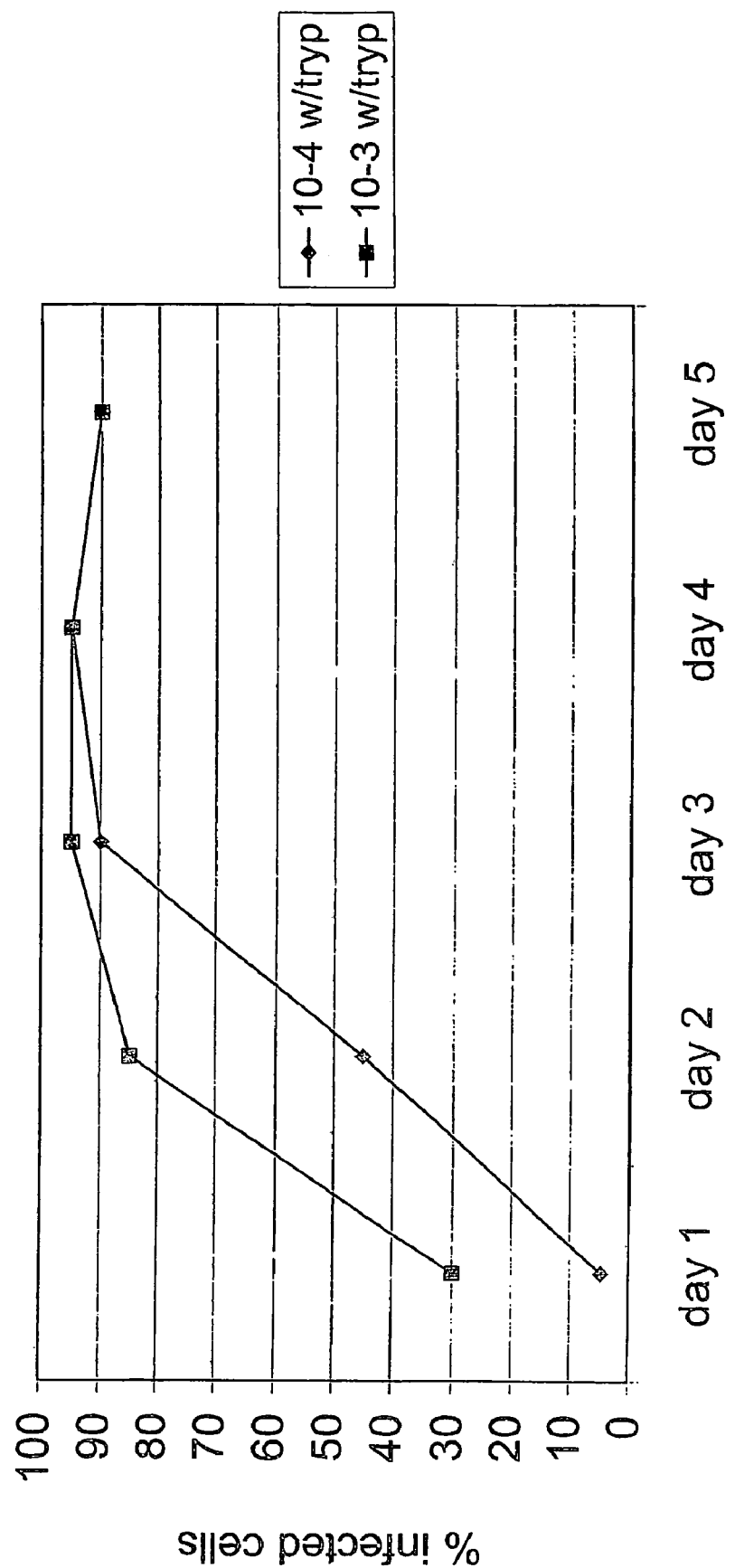

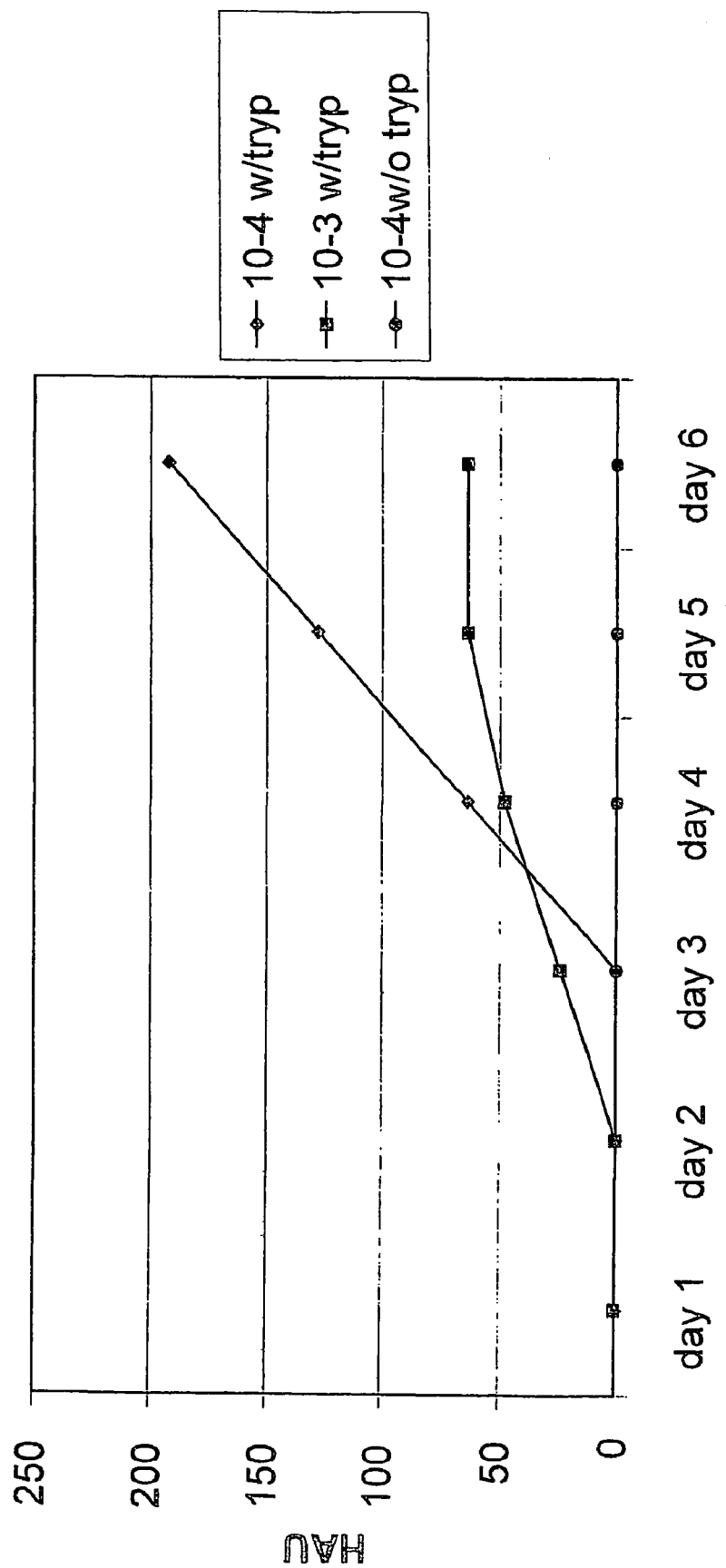

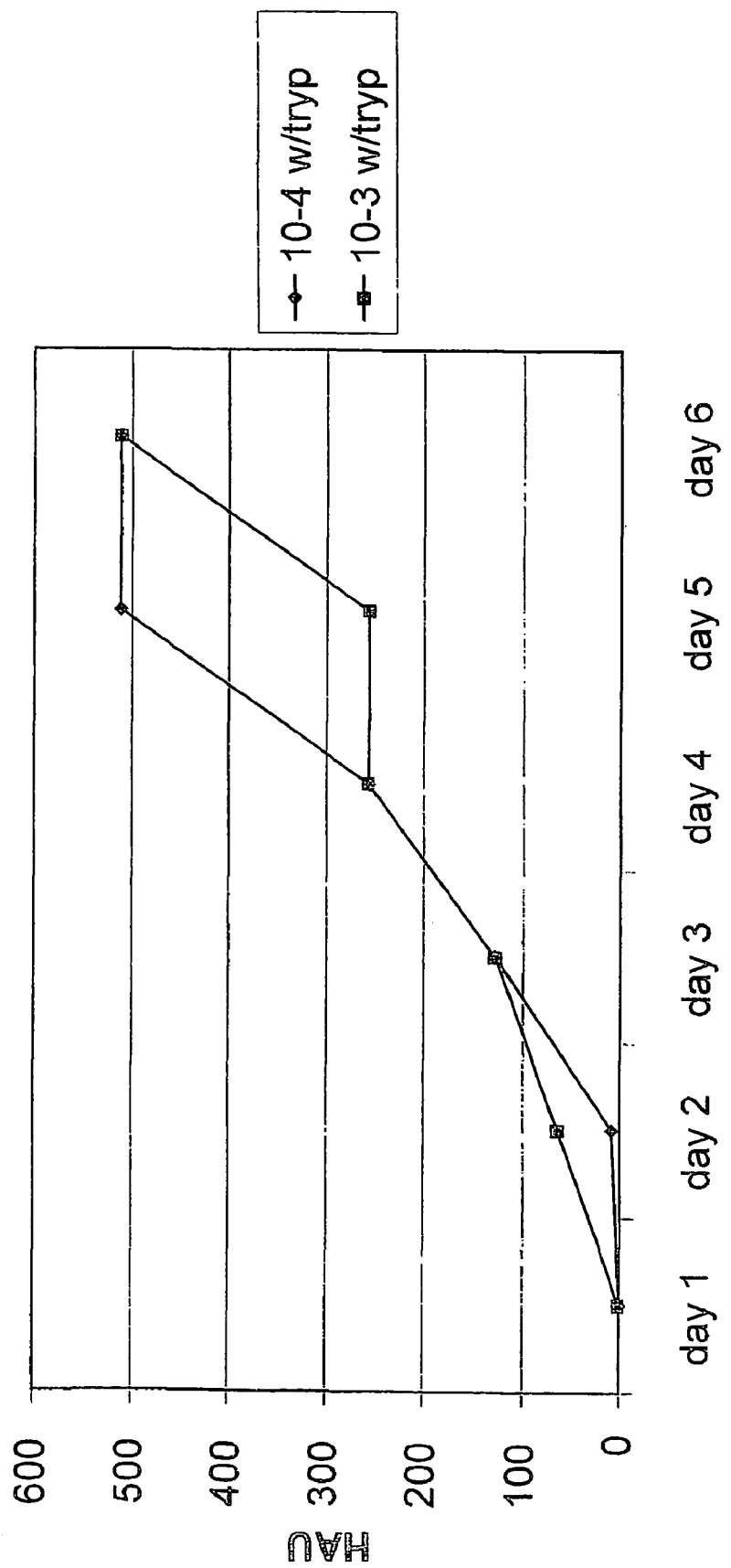

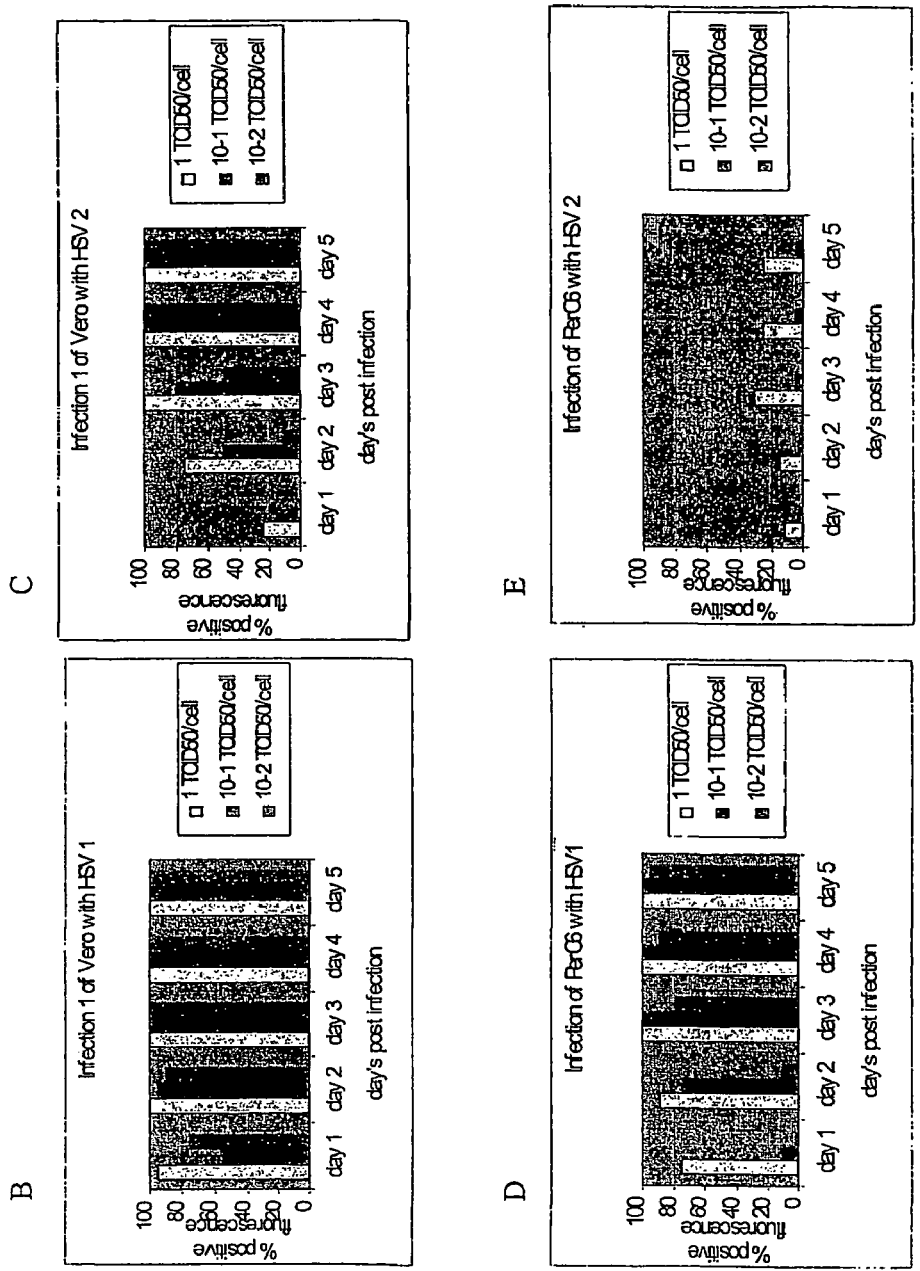
Figure 12 B - E

METHODS FOR THE IDENTIFICATION OF ANTIVIRAL COMPOUNDS

CROSS-REFERENCE TO RELATED APPLICATION

This application is a continuation of PCT International Patent Application No. PCT/NL02/00296, filed on May 6, 2002 and published, in English, on Nov. 14, 2002 as PCT International Publication No. WO 02/090982, the contents of the entirety of which are incorporated by this reference. This application also claims the benefit under 35 U.S.C. § 119(e) to U.S. provisional patent application 60/289,541 filed on May 7, 2002.

TECHNICAL FIELD

The invention relates generally to the field of biotechnology and microbiology. In particular, the invention relates to the field of identification of antiviral compounds.

BACKGROUND

Several procedures are known for treating virus-related diseases and for preventing disorders that arise as a consequence of viral infections. Prophylactic vaccination is probably one of the most effective measures against potential fatal infectious diseases, since an individual can become fully or partly protected against new infections. The immune system makes sure that the virus that has entered the body or cell is prevented from replicating in the individual, and in most cases the virus disappears completely from the system. Therapeutic vaccination refers to the treatment of infected individuals intentionally to prevent the virus from replicating further and consequently to halt disease progression or to cure the disease by eliminating the virus from the body.

Another way of dealing with viral infections is through the use of antiviral agents that either attack the viral particle directly or that prevent the infection, propagation, replication, packaging and/or growth of the virus in the individual. These treatments are applied either when the individual has already been infected and so a prophylactic vaccination is no longer necessary, or when an individual is at immediate risk to encounter an infection. Antiviral molecules inhibit certain processes and phases in the viral life cycle, thereby inhibiting the virus from spreading.

Several in vitro and in vivo methods for the identification of such antiviral compounds are known in the art. Methods that make use of the specific antiviral activity of certain compounds include the plaque reduction assay, the yield reduction assay, the virus antigen determination assay, the dye-uptake assay, the cytopathic effect (CPE) determination assay and several in vivo assays for virus replication. Many of the in vitro methods, especially the plaque reduction assay, have the major disadvantage that they cannot be applied in (very) high-throughput screens. Although the plaque reduction assay can be applied for most viruses that are known to date, it is necessary to inoculate large numbers of susceptible cells in suitable conditions with ranges of virus titers as well as large ranges of antiviral compound titers to detect the correct concentration of the compound that significantly decreases the number of plaques. This situation makes the plaque reduction assay very suitable for measuring the right concentration of a specific compound that affects the growth of a particular virus but very unsuitable for the identification of such (new and unknown) compounds in a library. Since many of the molecule libraries consist of a very large collection of separate compounds (>$10^{14}$ individual agents), it is required to have settings in which all separate compounds can be screened in a rapid and efficient manner with low costs. The other in vitro methods such as the yield reduction assay, the virus antigen determination assay, the dye-uptake assay and the cytopathic effect (CPE) determination assay are to a certain extent more suitable for high-throughput screening, but they clearly depend on the cell line that is used and whether such a cell line is able to grow in multi-well settings and for prolonged periods of time. Clearly, many of the primary cells that are used to determine the effect of an antiviral compound in plaque reduction assays cannot be cultured in high-throughput settings, since these cells do not grow indefinitely. Evidently, the in vivo antiviral methods, such as for example the ferret-, the mouse- and chicken models for influenza infection (reviewed by Sidwell et al. 2000) are useless for the identification of novel compounds that prevent virus-cell recognition and virus infection, replication, propagation and growth, especially when high-throughput settings are preferred.

Many susceptible non-continuous cells have been identified in which most viruses propagate. As mentioned, these cells can be used in assays such as the plaque reduction assay but cannot be applied for screening of antiviral compounds, since they do not either grow in multi-well formats or they do not grow indefinitely. Only a limited number of continuous cell lines have been identified that support the growth of certain viruses. These cell lines include the green monkey VERO cells, the Madin-Darby Canine Kidney ("MDCK") cells, the human lung embryo MRC-5 cells and the human A549 cells. However, a major drawback of these cells is that they only support the growth of a limited number of viruses, while not all of these cell lines are capable of continuous growth in multi-well formats. Nevertheless, a number of drugs displayed antiviral activities against viruses such as CMV, Influenza and HSV in the context of using the cells mentioned above. For example, Acyclovir, an approved purine nucleoside analogue, inhibited HSV replication in A549 cells (Li et al. 1988). Despite the few successful propagations of certain viruses on continuous cell lines and the prevention of propagation by a number of antiviral compounds, it was found that in many cases the cells did not support the complete life cycle of the mentioned viruses. This limits their use significantly in screening assays for antiviral compounds present in large libraries, because the life cycle of a virus is built up from several phases in which a compound can have its point of impact.

Although many cell-based systems exist that can be used to determine whether a particular compound is capable of preventing certain phases in the life cycle of a virus, no system is believed to be present in the art that combines the possibility of screening large numbers of (possible) antiviral compounds in a very high-throughput setting with the possibility of screening a large range of different viruses. No system is available in the art that combines these possibilities to determine the antiviral activity of a certain compound present in a compound library, in different phases of the life cycle of the particular virus that is attacked by this particular compound.

BRIEF SUMMARY OF THE INVENTION

The invention includes the use of cell lines that fully support the complete life cycle of a very wide variety of pathogenic viruses and that provide methods for screening libraries of antiviral compounds for identification of molecules with antiviral activity that can interfere with the pivotal processes in any phase of the life cycle of a pathogenic virus. The fact that these cell lines support the infection, replication, propagation and growth of a large variety of viruses is disclosed in PCT International Patent Application PCT/NL00/00862 (corresponding to PCT International Publication No. WO 01/38362), hereby incorporated in its entirety by this reference. PER.C6 cells are capable of growing in continuous cultures and have been cultured for over 200 passages. The fact that PER.C6 is suitable for high-throughput screenings is disclosed in PCT International Publication No. WO 99/64582.

The current invention deals with a large number of the problems and drawbacks known from the art concerning the identification of antiviral compounds using the assays and cell lines described above.

BRIEF DESCRIPTION OF THE SEVERAL VIEWS OF THE DRAWINGS

FIG. 2. Percentage of infected cells (positive cells) scored microscopically after immunofluorescence assay versus percentage of dead cells measured via FACS after propidium iodide staining, at moi's of $10^{-3}$ (A) and $10^{-4}$ (B). Poor viability of the cells from samples derived from infection at moi 10-3 did not give rise to reliable data.

FIG. 4. Percentage of infected cells (positive cells) viewed microscopically after immunofluorescence assay. (A) A/Beijing/262/95 and (B) X-127.

FIG. 5. Kinetics of virus propagation measured in HAU from day 1 to 6 after infection. (A) A/Beijing/262/95 and (B) X-127.

DETAILED DESCRIPTION OF THE INVENTION

Figure 1:
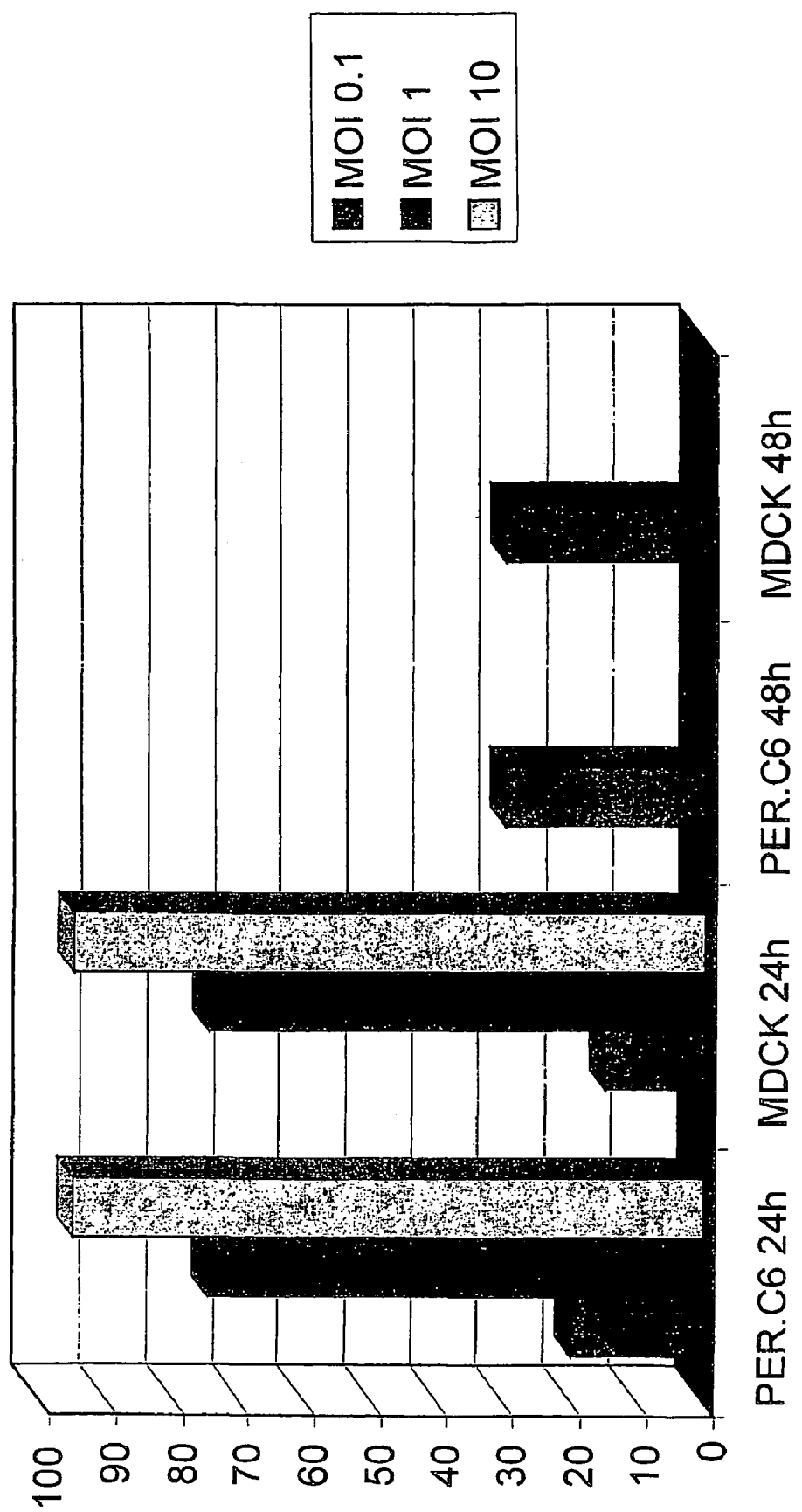
FIG. 1. Percentage of infected cells scored microscopically after immunofluorescence assay. Samples derived from infection at multiplicity of infection (moi) 10 and 1, at 48 h post infection are not shown, because of full CPE.

Disclosed herein are methods that substantially lack the above outlined drawbacks and being characterized in methods for identifying a compound and/or determining whether the compound influences a phase in the life cycle of a virus. The methods comprise providing a cell with the compound and with at least a fragment of the virus sufficient for performing the phase and determining whether the phase is influenced in the cell, the cell comprising a nucleic acid encoding an adenovirus early protein (or a functional part, derivative and/or analogue of the adenovirus early protein). It is to be understood that the compound can be provided before, after, and/or simultaneously with providing the fragment of the virus sufficient for performing the phase.

Preferably, the methods provided by the invention comprise a virus selected from the group of adenoviruses, enteroviruses, herpes viruses, orthomyxoviruses, paramyxoviruses, retroviruses, rotaviruses, coronaviruses, flaviviruses, togaviruses, hepatitis causing viruses, pestiviruses, rhabdoviruses and Bunyaviridae viruses. It will be clear to those skilled in the art that whenever a virus is identified that is able to perform one or more of its life-cycle phases in a cell, that the methods of the present invention can be applied.

In an even more preferred embodiment, the virus is an essentially intact virus, wherein 'essentially' means comprising an intact coat capable of recognizing and infecting an appropriate host cell, further comprising nucleic acid capable of supporting all required functions for normal replication, propagation, packaging and releasing newly formed virus particles.

In a preferred embodiment, the invention makes use of a human cell, the human cell being preferably derived from a kidney, retina or from amniotic fluid. In an even more preferred aspect of the invention, the human cell is transformed by an adenovirus early region 1 and/or -2 encoding nucleic acid, wherein the nucleic acid is preferably integrated in the genome of the cell.

The invention further provides methods for determining whether a compound influences a phase in the life cycle of a virus comprising providing a cell with the compound and with at least a fragment of the virus sufficient for performing the phase and determining whether the phase is influenced in the cell, the cell comprising a nucleic acid encoding an adenovirus early protein (or a functional part, derivative and/or analogue of the adenovirus early protein), wherein determining whether a compound influences a phase in the life cycle of a virus comprises examining the activity and/or amount of a cellular protein and/or examining the interaction of the virus with the cell and/or examining the activity and/or amount of the virus or a fragment thereof and/or examining the viability of the cell.

The invention is further characterized in uses of a cell, the cell comprising nucleic acid encoding an adenovirus early protein, such as early region 1 and/or -2, for screening a library of compounds for the presence of a compound capable of influencing a phase in the life cycle of a virus capable of entering the cell. In a preferred aspect of the invention, the uses of a cell comprise a virus selected from the group of adenoviruses, enteroviruses, herpes viruses, orthomyxoviruses, paramyxoviruses, retroviruses, rotaviruses, coronaviruses, flaviviruses, togaviruses, hepatitis-causing viruses, pestiviruses, rhabdoviruses and Bunyaviridae viruses. It will be clear to those skilled in the art that newly identified viruses or other viruses not mentioned in this list and that are able to perform one or more of its life-cycle phases in the cells, that the uses according to the present invention also apply to those viruses.

In a preferred embodiment, the compound is present as part of a compound library. In a more preferred embodiment, the compound library is used in high-throughput settings. In an even more preferred embodiment, the method comprises isolating the compound. The invention provides methods for screening (anti-viral) compound libraries using cells, viruses and methods of the present invention.

In another aspect, the invention provides methods for identifying a compound with antiviral activity comprising providing a cell from a first collection of cell cultures with at least a fragment of a first virus, the fragment capable of performing a phase in the life cycle of the first virus, providing the cell from a first collection of cell cultures with a compound and determining whether the compound is capable of influencing the phase in the life cycle of the first virus, the method further comprising providing a cell from a second collection of cell cultures with at least a fragment of a second virus, the fragment capable of performing a phase in the life cycle of the second virus, providing the cell from a second collection of cell cultures with a second compound and determining whether the second compound is capable of inhibiting the phase in the life cycle of the second virus, wherein the cells from the first and the second collection comprise a nucleic acid encoding an adenovirus early protein and wherein the first and the second library of compounds may be the same or different.

In another aspect, the invention provides methods for determining the effect of a compound on a phase in the life cycle of a virus comprising the steps of culturing a cell, the cell otherwise capable of supporting the phase in the life cycle of a virus, in the presence of the virus under conditions otherwise conducive to the phase in the life cycle of the virus and in the absence of the compound, examining the effect of the absence of the compound on the phase in the life cycle of the virus. Preferably, the compound is a natural constituent of the cell. More preferably, the natural constituent is a receptor protein, or a fragment thereof, for the virus. Even more preferably, the cell is comprised in a set of clones of cells or a library of cells, the cells comprising a gene being effectively blocked from being expressed, wherein "effectively blocked" is defined as significantly reduced.

In an even more preferred aspect of the invention, the cell comprises a nucleic acid encoding an adenovirus early protein (e.g., such as early region-1 and/or -2).

As used herein, "adenovirus early protein" includes a functional part, derivative and/or analogue of an adenovirus early protein having the activity of adenovirus early protein (e.g., such as early region-1 and/or -2) in the methods of the invention.

The "phase in the life cycle of a virus" is defined as a phase that can comprise a step or a period during which a virus recognizes its host cell or during which the virus interacts with its host cell through a protein, preferably a protein expressed by the host cell. The phase in the life cycle of a virus is further defined as a phase that can comprise a step or a period during which a virus infects (enters) a cell, replicates its nucleic acid with or without using cellular factors, and produces the required proteins in the cell for propagation and/or packaging of the newly made viral particle(s) in the cell. A life cycle of a virus can be generally defined as (a) recognition and/or interaction of the virus with a host cell,
(b) entering (infecting) the host cell,
(c) changing the host cell environment to enable a generation of new virus particles, for instance by expression of viral proteins from the infected nucleic acid,
(d) replication of the nucleic acid,
(e) expression of viral proteins required for packaging new viral particles,
(f) packaging of new viral particles, and
(g) release of the newly formed particles from the infected cell, wherein these phases can occur sequentially or simultaneously and wherein several sub-phases might be distinguished.

To determine to what extent a certain compound influences a specific phase in the life cycle of a virus, several methodologies can be applied. Examples of such methodologies are (1) measuring the levels and/or activities of viral and/or cellular proteins that are present upon entry of the virus into the host cell, (2) examining the recognition of the virus with the host cell or the interaction of the virus with the host cell and/or host cell proteins, (3) examining the activity and/or amount of the virus or a fragment thereof and (4) examining the viability of the infected host cell.

The viruses used by the present invention to screen for antiviral compounds include adenovirus, enterovirus (such as rhinovirus, aphtovirus, or poliomyelitisvirus), herpes virus (such as herpes symplex virus, pseudorabies virus or bovine herpes virus), orthomyxovirus (such as influenza virus), paramyxovirus (such as Newcastle disease virus, respiratory syncitio virus, mumps virus or measles virus), retrovirus (such as human immunodeficiency virus), parvovirus, papovavirus, rotavirus, coronavirus (such as transmissable gastroenteritis virus), Flavivirus (such as tick-borne encephalitis virus or yellow fever virus), togavirus (such as rubella virus or Eastern-, Western-, or Venezuelean Equine Encephalomyelitis virus), hepatitis causing virus (such as hepatitis A, -B or -C virus), pestivirus (such as hog cholera virus), rhabdovirus (such as rabies virus) or Bunyaviridae virus (such as Hantavirus).

The invention relates to the identification of antiviral compounds directed against viruses or viral pathogens that previously could not or poorly be grown on human cells in vitro. The invention is particularly useful for the production of therapeutics to aid in protection against viral pathogens for vertebrates, in particular mammalians and especially humans.

The invention discloses methods and means for the identification and/or validation of compounds harboring antiviral activities and the like that interfere with the life cycle of viral pathogens. The identification and/or validation can either be performed in low-throughput, medium-throughput, high-throughput or ultra high throughput settings, ranging from a few compounds to >$10^{14}$ compounds present in a library of compounds. The invention relates to the screening of compound libraries comprising non-proteinaceous substances like small or large (synthetic) compounds such as nucleoside analogues or nucleic acid such as DNA molecules. The invention also relates to the screening of compound libraries comprising molecules like proteinaceous substances such as peptides, antibodies, hormones, receptors or other protein binding entities or fragments thereof. The non-proteinaceous substances, proteinaceous substances in such collections can be expressed on phage particles or can be present as separate molecules not expressed on phage particle. The invention moreover relates to the screening of compound libraries comprising large particles like viruses, virus particles, phage and fragments thereof. The compounds can have already known- or yet undiscovered functions for antiviral activity.

The invention is particularly useful for the identification of molecules that interfere with infection of cells by viral pathogens, binding and/or entry of viral pathogens into cells, replication of the viral pathogens in cells, packaging of viral pathogens into viral particles and/or release of the viral pathogens from cells and/or re-infection of cells by such viral pathogens, to aid in protection against viral pathogens for vertebrates, in particular mammalians and especially humans.

The invention relates to the use of mammalian cells, preferably a non-tumor-derived transformed human cell for the screening of such libraries of molecules. More preferably the invention makes use of a human non-tumor derived cell that is transformed with early proteins of Adenovirus. Even more preferred is the use of human cells that are not derived from tumors and that are transformed with early region E1 from adenovirus, such as the human embryonic retina derived PER.C6™ cells (deposited with the ECACC. European Collection of Cell Cultures, Salisbury, Wiltshire, SP4 OJG UK, on Feb. 29, 1996 under accession number 96022940). The present invention discloses human immortalized cell lines (PER.C6 and derivatives thereof) that are generally used for the production of recombinant adenoviral vectors and for the purpose of propagating, production and harvesting viruses other than adenovirus to generate vaccines (disclosed in PCT International Patent Application No. PCT/NL00/00862, corresponding to PCT International Publication No. WO 01/38362). The PER.C6 cells were generated by transfection of primary human embryonic retina cells, using a plasmid that contained the Ad serotype 5 (Ad5) E1A- and E1B-coding sequences (Ad5 nucleotides 459-3510) under the control of the human phosphoglycerate kinase (PGK) promoter.

The following features make PER.C6 and derivatives thereof particularly useful as a host for virus production: it is a fully characterized human cell line, it was developed in compliance with GLP, it can be grown as suspension cultures in defined serum-free medium, devoid of any human or animal serum proteins; its growth is compatible with roller bottles, shaker flasks, spinner flasks and bioreactors, with doubling times of about 35 h. Moreover, it was found that PER.C6 were very suitable for growth in multi-well settings and for the propagation of adenoviruses in high-throughput methodologies (PCT International Publication No. WO 99/64582).

The invention provides the use of such cell lines for the identification of novel antiviral compounds that act towards viruses for which no known antiviral compounds were thus far identified. Moreover, the invention enables the identification of known antiviral compounds, which also act upon viruses that could not, thus far, be propagated on cell lines used in the art. Such known and unidentified antiviral compounds (often small molecules) can either be rationally designed or identified in screenings assays. The antiviral strategies that these compounds employ are sometimes known (e.g., neuraminidase inhibitors for treatment of influenza infection and DNA synthesis inhibitors for the treatment of HSV infection). On the other hand, many drugs have been developed that exert an antiviral effect in patients through mechanisms that are not completely understood. Many such drugs were identified in recent years.

For example, the protein Interferon alpha is used for the treatment of HCV infected patients. It is applied alone or in combination with Ribavirin (Keating 1999), although problems have occurred for HCV treatment when used alone (Polyak et al. 2000). Famciclovir and valaciclovir are two approved compounds and that are used for Herpes Simplex Virus (HSV) and for varicella-zoster infections (Keating 1999). Ganciclovir (GCV), a purine nucleoside analogue was approved to treat CMV retinitis (Keating 1999; Alrabiah et al. 1996), while another approved purine nucleoside analogue, acyclovir (ACV) is being applied for genital herpes, HSV encephalitis, mucocutaneous herpetic infections, varicella-zoster and for herpes-zoster infections (Keating 1999; Dwyer et al. 1997). Two nucleoside phosphonate analogues, Adefovir and Tenofovir, are being used to treat HBV infections (Ying et al. 2000). The compound Dibenzofuran was found to block rhinovirus replication in vitro and to hinder the cytopathic effect in cells infected with HRV14 or HRV16 (Murray et al. 1999). In recent years several protease inhibitory agents were identified that were active against the Human Immunodeficiency Virus (HIV): Saquinavir (Figgitt et al. 2000) and Nelfinavir (Bardsley-Elliot et al. 2000a). Nevirapine is an approved non-nucleoside Reverse Transcriptase inhibitor (NNRTI) used against HIV infections (Bardsley-Elliot et al. 2000b), while a non-nucleoside RT inhibitor (NNRTI), Delavirdine (a bishet-eroarylpiperazine derivative) was also found to be active against HIV (Scott et al. 2000; Joly et al. 2000). Amantidine and Rimantadine are two drugs that are used for the treatment of Influenza A infections (Keating 1999). Nucleoside analogues are reviewed by Pastor-Anglada et al. (1998) and the idea to use protease inhibition to attack virus infections is discussed by Todd et al. (2000). This list of antiviral agents is by far not limiting and many proteins, small molecules and other types of compounds are still in several different phases of development.

Although the PER.C6 cell line was developed for the production of recombinant adenoviral vectors (mainly derived from adenovirus serotype 5, or Ad5) through the complementation of E1 deleted vectors by the E1 functions provided by the integrated E1-expressing plasmid, it was also found that PER.C6 cells were able to support the production of exogenous proteins such as recombinant human erythropoietin ("EPO") or human monoclonal antibodies encoded by expression plasmids that were transfected and integrated stably or that were present in a transient system (PCT International Publication No. WO 00/63403). Besides Ad5, PER.C6 is also able to support the growth of every other wild-type adenoviral serotype found to date (a total of 51 adenovirus serotypes, disclosed in European patent application publication number EP 0978566).

Interestingly, PER.C6 also supports the growth of an entire different set of viruses besides adenoviruses. Examples of these viruses are, but are not limited to, Human- and Duck Influenza virus, Human- and Rhesus Rotavirus, Measles Virus, Respiratory Syncytium virus A and B, Parainfluenza types -1, -2 and -3, Poliovirus types -1, -2 and -3, Coxsackie virus B2, B4, A9, Echovirus types -4, -7 and -11, Japanese encephalitis virus, Hantavirus and Herpes Simplex Virus types -1 and -2. Examples of such viruses that can grow on PER.C6 are disclosed herein and in PCT/NL00/00862 (PCT International Publication No. WO 01/38362; incorporated herein by reference).

For example, rotaviruses can grow on PER.C6 cells. Rotaviruses, members of the family of Reoviridae, are double strand RNA viruses consisting of 11 RNA segments, each coding for a structural or non-structural viral protein (VP). Given the worldwide prevalence of rotavirus associated infant morbidity and mortality, large scale vaccination against rotavirus is thus far considered the most effective way to combat this virus. The goal of vaccination would not be to prevent the disease but to reduce its severity and complication, especially during the first few years of life. The only vaccine at present is a live attenuated orally delivered composition that is associated with intussuception, a bowel obstruction disease. For that reason, this vaccine is no longer in use. It is evident that there is a need for anti-rotavirus drugs that can be used to treat Rotavirus infected patients. The identification of such drugs was thus far hampered by the difficulty of growing the virus in suitable systems. The present invention provides methods of using a human cell line that is highly capable of supporting infection, replication, propagation and growth of rotavirus, thereby providing a system for the identification of compounds that prevent rotavirus generation in human cells using a multi-well set up.

Adenoviruses are another set of viruses for which the present invention provides the possibility to identify antiviral compounds against. Although adenoviruses are known to cause minor disorders such as common colds, it is also known that in immuno-suppressed patients adenoviruses can cause severities that can even lead to death of such patients. Of all bone-marrow transplant patients that die during or after treatment, approximately 20% die of an adenovirus infection. Clearly, there is a great need for anti-adenoviral compounds that can prevent the occurrence of malignancies due to adenoviral infections in these patients that have a suppressed immune response.

To further illustrate the invention, the following experimental procedures and illustrative examples are provided, not intended to limit the scope of the invention.

EXAMPLES

Experimental Procedures

PER.C6 and MDCK Cell Culture

Madin-Darby Canine Kidney (MDCK) cells and PER.C6™ cells (deposited under No. 96022940 at the ECACC, described in PCT International Publication No. WO 97/00326 and U.S. Pat. No. 6,033,908) were cultured in Dulbecco's modified Eagle's medium (DMEM, Life Technologies) containing 10% heat inactivated fetal bovine serum and 1× L-Glutamin (Gibco), at 37° C. and 10% $CO_2$. Suspension cultures of PER.C6 were cultured in ExCell 525 (JRH Biosciences) supplemented with 1× L-Glutamin, at 37° C. and 10% $CO_2$, in stationary cultures in 6 well dishes (Greiner) or in 490 $cm^2$ tissue culture roller bottles (Corning Costar Corporation) during continuous rotation at 1 rpm.

Immunofluorescence Test

Direct immunofluorescence assays for the detection of Influenza virus infection were carried out using the IMAGEN™ Influenza Virus A and B kit (Dako) according to the standard protocol of the supplier. Samples were viewed microscopically using epifluorescence illumination. Infected cells were characterized by a bright apple-green fluorescence.

Propidium Iodide Staining

Cell pellets were resuspended in 300 µl of cold PBS/0.5% BSA+5 µl of propidium iodide (concentration 50 µg/ml) in PBS/FCS/azide solution known to persons skilled in the art. Viable and dead cells were then detected via flow cytofluorometric analysis.

Haemagglutination Assay

In general, haemagglutination assays for influenza virus titers were performed according to methods known to persons skilled in the art. Here, 50 µl of a two-fold diluted virus solution in PBS was added to 25 µl PBS and 25 µl of a 1% suspension of turkey erythrocytes (Biotrading Benelux B.V.) in PBS and incubated in 96 well microtiter plates at 4° C. for 1 h. The haemagglutination pattern was examined and scored, and expressed as hemagglutinating units (HAU's). The number of HAU's corresponded to the reciprocal value of the highest virus dilution that showed complete haemagglutination.

Western Blot Analysis of the Influenza HA Protein

In general, obtained influenza viruses were disrupted in a Laemmli buffer according to methods known to persons skilled in the art and different volumes of obtained protein mixtures were separated using 10% SDS/PAGE gels. In brief, blots were blocked for 30 min at room temperature with block solution (5% non fat dry milk powder (Biorad) in TBST supplemented with 1% rabbit serum (Rockland)), followed by 3 washes with TBST. Then, the blots were incubated with the anti A/Sydney/5/97 HA antiserum (98/768 NIBSC) diluted 1/500 in 1% BSA/TBST with 5% rabbit serum (Rockland) O/N at room temperature. Again, the blots were washed 8 times with TBST. Finally the blots were incubated with the rabbit anti sheep antiserum (HRP labeled, Rockland) 1/6000 diluted in block solution for 1 h at room temperature. After 8 washes with TBST, the protein-conjugate complex was visualized with ECL (Amersham Pharmacia Biotech), and films (Hyperfilm, Amersham Life Science) were exposed. The antisera were obtained from the NIBSC (UK) and applied in dilutions recommended by the NIBSC.

Single Radial Immunodiffusion (SRID) Assay

The concentration of haemagglutinin in supernatants, derived from influenza virus infected-PER.C6 cells, was determined by the single radial immunodiffusion (SRID) test as previously described (Wood et al. 1977). The assay was performed using standard NIBSC (UK) antigens and antisera reagents.

Plaque Assay

A total of 1 ml of 10-fold serially diluted viral supernatants were inoculated on MDCK cells which were grown until 95% confluence in 6-well plates. After 1 h at 35° C., the cells were washed twice with PBS and overloaded with 3 ml of agarose mix (1.2 ml 2.5% agarose, 1.5 ml 2×MEM, 30 µl 200 mM L-glutamine, 24 µl trypsin-EDTA, 250 µl PBS). The cells were then incubated in a humid, 10% $CO_2$ atmosphere at 35° C. for approximately 3 days and viral plaques were visually scored.

Virus Infectivity Assay ($TCID_{50}$)

Titration of infectious virus was performed on MDCK cells. In brief, cells were seeded in 96 well plates at a density of $4 \times 10^4$ cells/well in DMEM supplemented with 2 mM L-Glutamin. Twenty-four hours later, cells were infected with 100 µl of ten fold serially diluted culture supernatants, in quadruplicate, in medium containing trypsin-EDTA at a concentration of 4 µg/ml. Two hours after infection, cell monolayers were washed two times in PBS and incubated in medium containing trypsin for 7 days, at 35° C. Supernatants from these cultures were then tested in an HA assay. $TCID_{50}$ titers were calculated according to the method of Karber (1931), which is well known to persons skilled in the art.

Example 1

PER.C6 Cells as Permissive Cell Line for Influenza A Virus

It was not known prior to the invention described in PCT/NL00/00862 (PCT International Publication No. WO 01/38362), that PER.C6™ as a human cell could sustain influenza virus infection and replication. It was verified whether PER.C6 cells are permissive for influenza virus infection in comparison with the dog cell line MDCK, which served as a positive control.

On the day before infection, $2 \times 10^5$ MDCK cells per well were seeded in 6-well plates. Twenty-four hours later, $4 \times 10^5$ seeded PER.C6 and the MDCK cells per well were infected with the H1N1 strain A/Puerto Rico/8/34 (titer $3.6 \times 10^7$ pfU/ml), (obtained from Dr. E. Claas, Leiden University Medical Centre, NL). Infection was performed at various multiplicities of infection (moi's) ranging from of 0.1 to 10 pfu/cell. After about 2 h of incubation at 37° C., the inoculum was removed and replaced by fresh culture medium. A direct immunofluorescence assay for the detection of Influenza virus infection was performed 24 h and 48 h post infection. The experiment showed permissiveness of PER.C6 for Influenza infection, with percentages of positive cells moi-dependent and comparable with MDCK (FIG. 1).

Example 2

PER.C6 Used for Influenza A Virus Propagation

Figure 3:
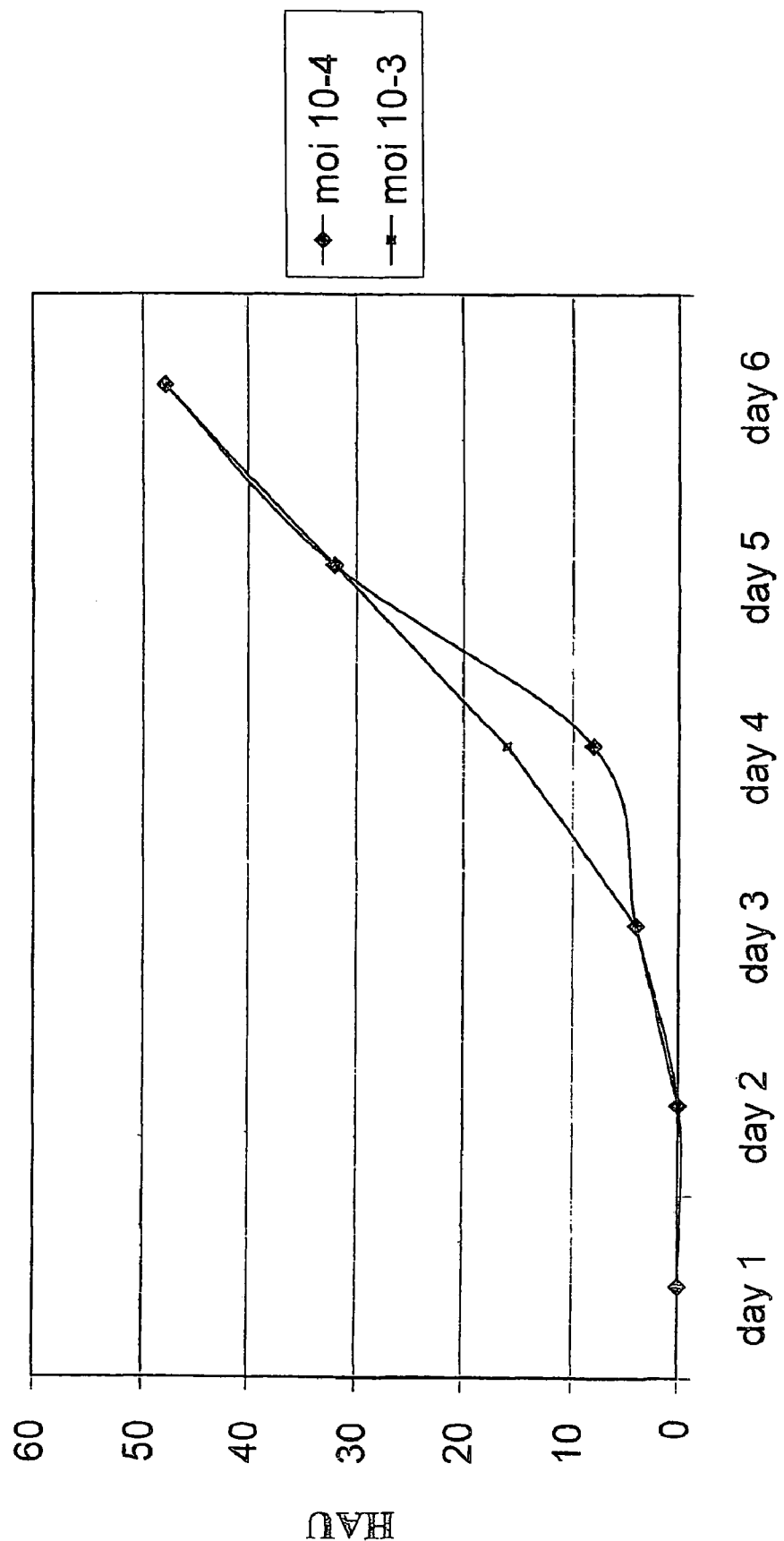
FIG. 3. Kinetics of virus propagation measured in hemagglutinating units (HAU) from day 1 to day 6 after infection.

It was verified whether or not only permissiveness, but also replication and propagation of Influenza virus could be supported by PER.C6. On the day of infection, PER.C6 cells were seeded in 490 $cm^2$ tissue culture roller bottles, with the density of $2 \times 10^5$ cells/ml in a final volume of 40 ml, in the presence of 5 µg/ml of trypsin-EDTA (Gibco-BRL). Cells were either mock inoculated or infected with the H3N2 strain A/Shenzhen/227/95 (titer $1.5 \times 10^6$ pfU/ml) (obtained from Dr. E. Claas, Leiden University Medical Centre, NL). Infections were performed at moi $10^{-4}$ and $10^{-3}$ pfu/cell. After 1 h of incubation at 37° C., the inoculum was removed by spinning down the cells at 1500 rpm and resuspending the cells in fresh culture medium +5 µg/ml of trypsin-EDTA. Harvest of 1.3 ml of cell suspension was carried out each day, from day 1 to day 6 post-infection. Supernatants were stored at −80° C. and used for haemagglutination assays. Cell pellets were used for direct immunofluorescence tests and for propidium iodide staining. Results of these experiments are shown in FIG. 2 and FIG. 3, respectively.

Example 3

Permissiveness of PER.C6 for Different Influenza Strains

To further investigate the permissiveness of PER.C6 for propagation of various influenza strains, an infection by using the H1N1 vaccine strains A/Beijing/262/95 and its reassortant X-127, obtained from the National Institute for Biological Standards and Control (NIBSC, UK) was performed. On the day of infection, PER.C6 cells were seeded in 490 $cm^2$ tissue culture roller bottles, with the density of approximately $1 \times 10^6$ cells/ml in a final volume of 50 ml. Cells were inoculated with 5 µl ($10^{-4}$ dilution) and 50 µl ($10^{-3}$ dilution) of virus in the presence of 5 µg/ml trypsin-EDTA. In order to establish if trypsin was indeed required, one more infection was carried out by inoculating 5 µl of the strain A/Beijing/262/95 in the absence of the protease. After approximately 1 h of incubation at 37° C., the inoculum was removed by spinning down the cells at 1500 rpm and resuspending them in fresh culture medium +5 µg/ml of trypsin-EDTA. At day 2 and day 4 post-infection, more trypsin was added to the samples. Harvest of 1.3 ml of cell suspension was carried out from day 1 to day 6 post-infection. Supernatants were stored at −80° C. and used for haemagglutination assays and further infections; cell pellets were used for direct imunofluorescence tests. Results obtained with the above-mentioned imnmunofluorescence and haemagglutination assays are shown in FIG. 4 and FIG. 5, respectively, illustrating the efficient replication and release of the viruses.

Example 4

Effect of Different Concentrations of Trypsin-EDTA on the Viability of PER.C6 Cells, on the Influenza Virus Production in PER.C6 Cells and on the HA Protein Derived thereof Due to the absolute trypsin requirement for the propagation of influenza virus in cell cultures, the effects of different concentrations of trypsin-EDTA on PER.C6 cell viability and virus replication in PER.C6 cells, after infection with several influenza strains, were investigated.

Infection with Influenza Virus Strain A/SYDNEY/5/97 in the Presence of Low Concentrations of Trypsin On the day of infection, PER.C6 cells were seeded in 490 cm$^2$ tissue culture roller bottles, at a density of 1×10$^6$ cells/ml, in the presence of trypsin-EDTA at final concentrations of 0.5, 1, 2, 3 and 5 µg/ml.

Figure 6:
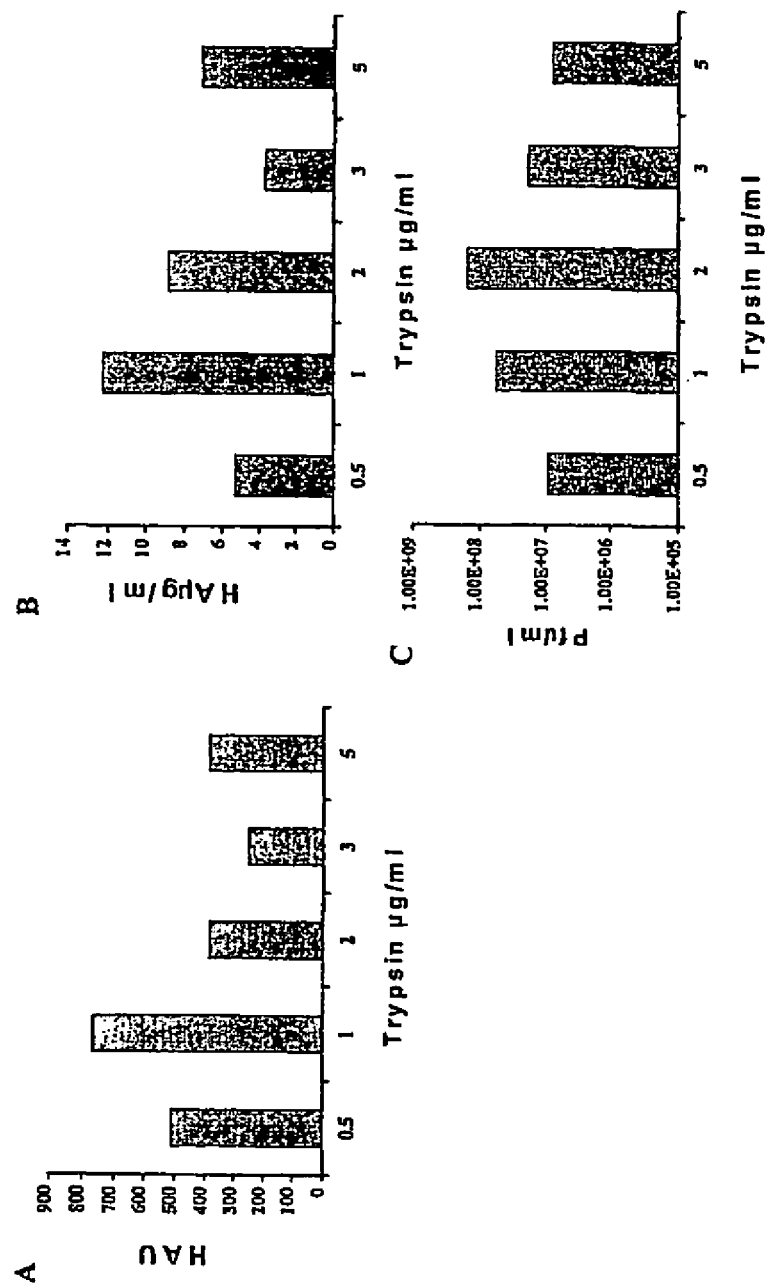
FIG. 6. Infection with A/Sydney/5/97 on PER.C6. (A) Effect of trypsin-EDTA on HAU titers. (B) HA concentration in µg/ml and (C) virus infectivity titers in plaque forming units per ml (pfu's/ml) as measured in crude viral supernatants, 96 hours post infection.

These trypsin concentrations did not interfere with the growth characteristics of the cells and their viability (data not shown). Cells were either, mock infected or infected with PER.C6-grown influenza virus A/Sydney/5/97 at an moi of 10$^{-4}$ pfu/cell. The viral production was monitored by direct immunofluorescence (data not shown), haemagglutination assays, single-radial-immunodiffusion (SRID) and plaque assays, all as described above. Results from this experiment are depicted in FIG. 6 and show that the HA content as measured by SRID as well as the biological activity of the virus, expressed in HAU, were highest when a trypsin concentration of 1 µg/ml was used. FIG. 6 also shows that by using a plaque assay the highest number of plaque forming units (pfu) per ml was observed in the sample corresponding to cells grown in medium containing 2 µg/ml of trypsin.

Infection with Influenza Virus Strain B/HARBIN/7/94

Figure 7:
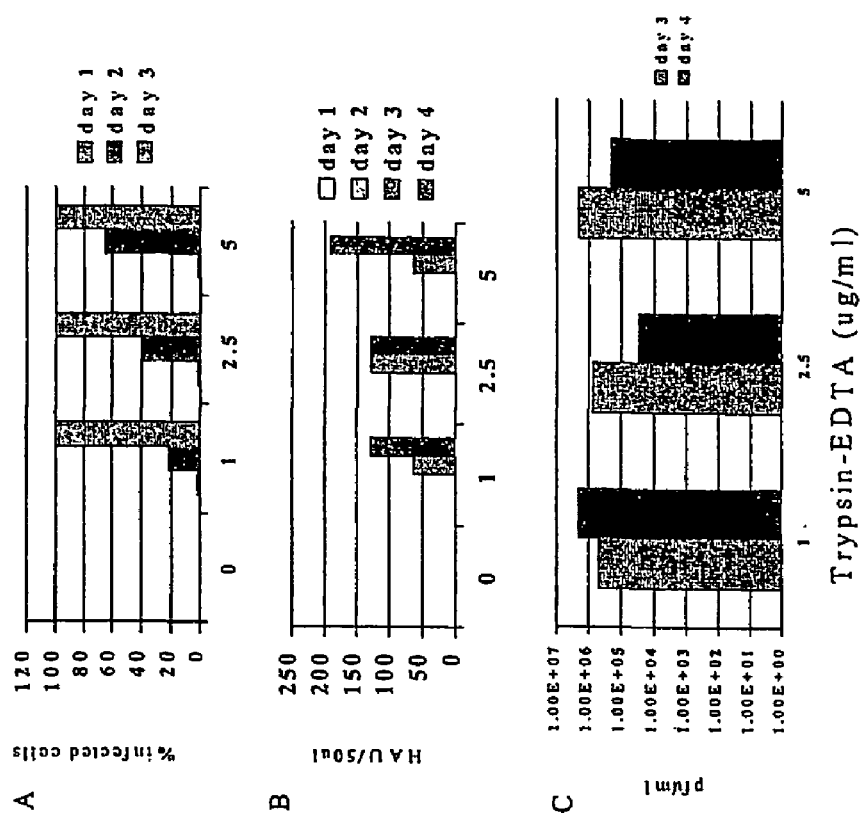
FIG. 7. Infection with B/Harbin/7/94 on PER.C6. (A) Effect of different concentrations of trypsin-EDTA present during and after virus infection on growth kinetics. (B) HAU titers per 50 µl and (C) virus infectivity titers in pfu/ml.

On the day of infection PER.C6 cells were seeded in 490 cm$^2$ tissue culture roller bottles at a density of 1×10$^6$ cells/ml, in the presence of different concentrations of trypsin-EDTA, ranging from 1 to 5 µg/ml. Cells were infected with PER.C6-grown virus B/Harbin/7/94 at an moi of 10$^{-3}$ pfu/cell. Production of the virus was monitored by direct immunofluorescence, haemagglutination and plaque assays as shown in FIG. 7. The infectability of PER.C6 at day 2 increased with the concentration of trypsin. At day 3, however, no significant difference was observed in the percentage of infected cells when 1, 2.5 or 5 µg/ml trypsin was present. In the absence of trypsin (0 µg/ml), no influenza virus infection was detected. At the day of the last harvest (day 4 post-infection), the biological activity of the virus, as measured by haemagglutination assay, did not differ significantly. Interestingly, the infectivity assay performed in samples that were taken at day 3 and 4 after infection, showed a difference in the production of the virus. The highest titers were obtained at day 3 and day 4 when a trypsin concentration of 2.5 to 5 (day 3) and 1 pg/ml (day 4) were used.

Infection with Influenza Virus Reassortment X-127

Figure 8:
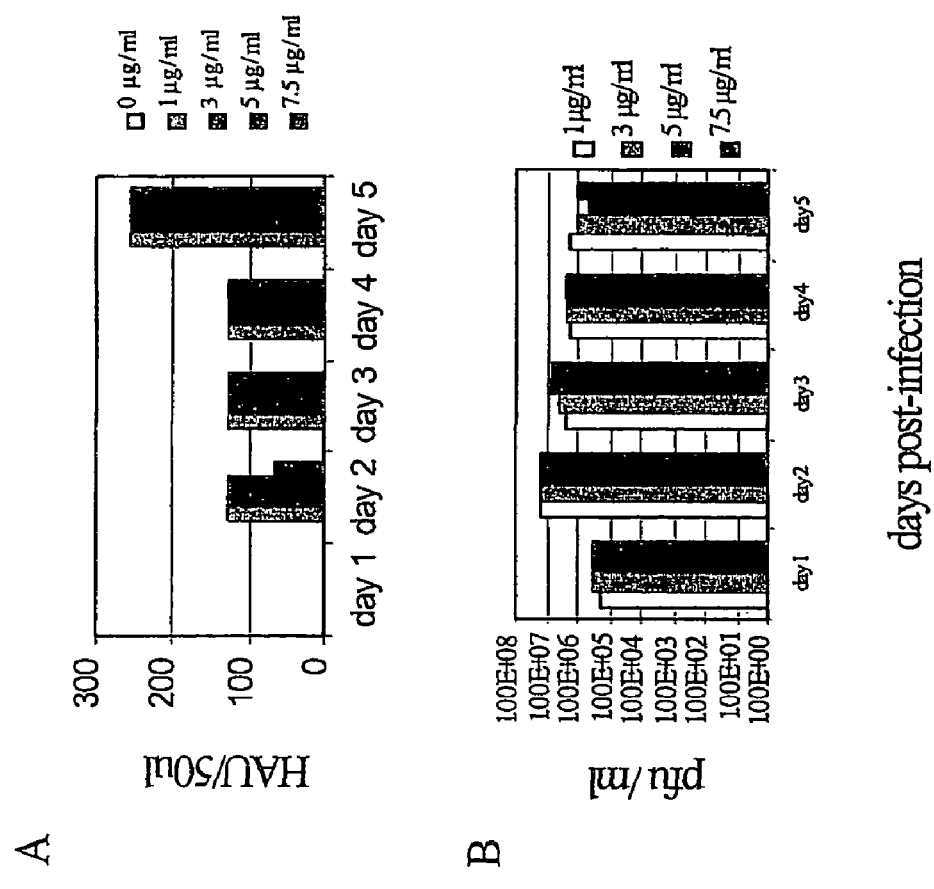
FIG. 8. Infection with X-127 using an moi of $10^{-3}$ on PER.C6. (A) Effect of trypsin-EDTA on HAU given in HAU/50 µl and (B) virus infectivity titers in pfu/ml during 5 days after infection.
Figure 9:
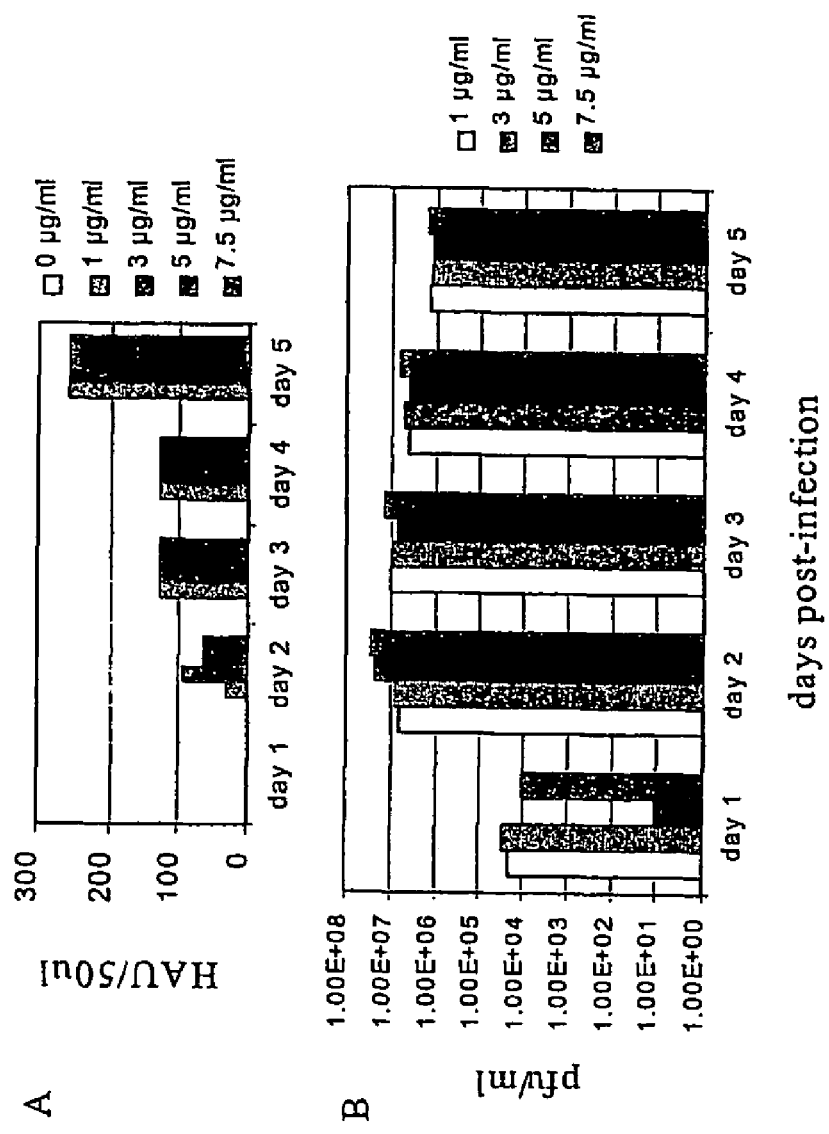
FIG. 9. Infection with X-127 using an moi of $10^{-4}$ on PER.C6. (A) Effect of trypsin-EDTA on HAU given in HAU/50 µl and (B) virus infectivity titers in pfu/ml during 5 days after infection.

On the day of infection, PER.C6 cells were seeded in T25 tissue culture flasks, at a density of 1×10$^6$ cells/ml, in the presence of different concentrations of trypsin-EDTA ranging from 0 to 7.5 µg/ml. Cells were infected with PER.C6-grown virus X-127 (egg-reassortant for the strain A/Beijing/262/95) at an moi of 10$^{-4}$ and 10$^{-3}$ pfu/cell. Viral growth was monitored by direct immunofluorescence, haemagglutination and plaque assays. As shown in FIG. 8 and FIG. 9, HAU titers were identical between samples, independent of the trypsin concentration and the initial moi that was used. Furthermore, no significant differences were observed in the infectivity titers, as measured by plaque assay.

Example 5

Electron Microscopy Analysis of Influenza Viruses on PER.C6 Cells

Figure 10:
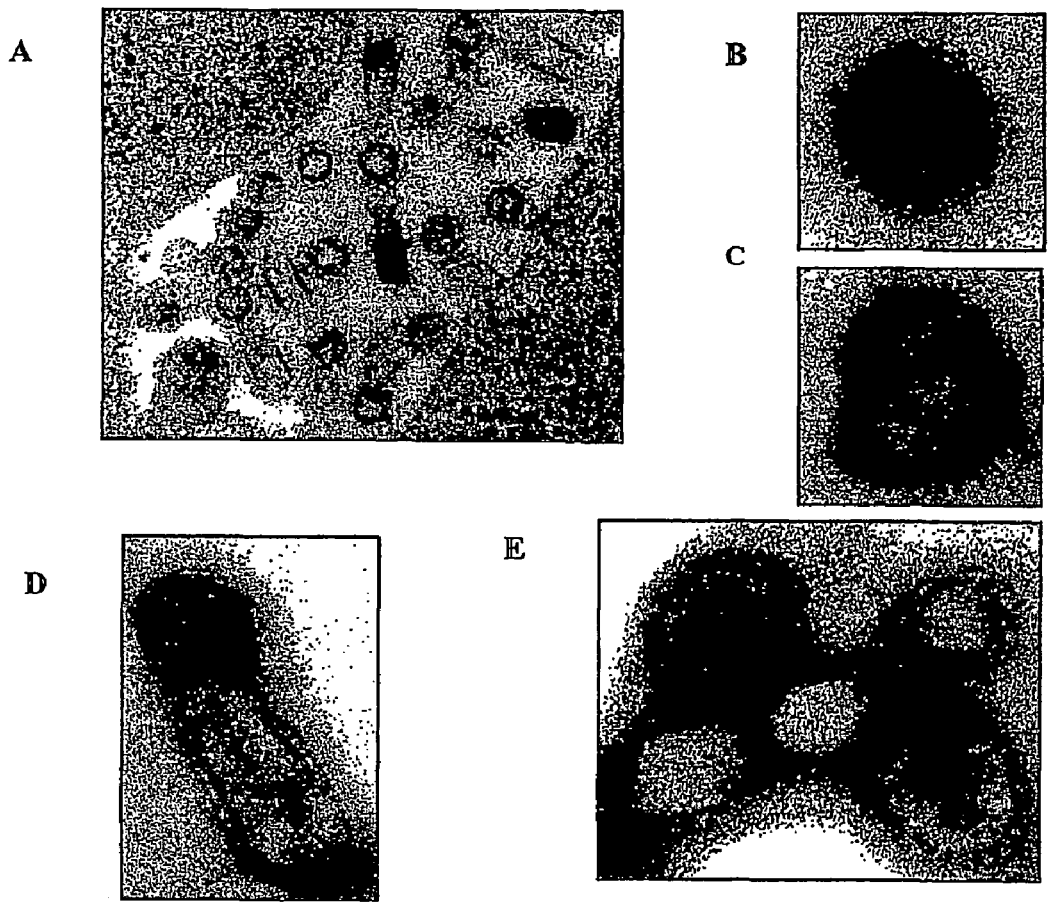
FIG. 10. Electron micrographs of Influenza A/Sydney/5/97. (A) ER.C6 cells 72 hrs post infection. (B and C) Negative staining on virus derived from infected PER.C6. (D and E) Negative staining of sucrose purified material.

Transmission electron microscopy studies were done on PER.C6 cells that were infected with the Influenza strain A/Sydney/5/97 as well as on viral containing supernatants and sucrose purified material to determine the phenotype of this influenza virus produced on PER.C6. All methods that were used are well known to persons skilled in the art. FIG. 10 shows that the last stages of the virus life cycle are represented by budding and release of enveloped virions from the cytoplasmic membrane. Spikes corresponding to the HA and NA viral proteins were detected, ornamenting the periphery of the virion particles. The figure also shows the characteristic pleiomorphism of influenza viruses.

Example 6

Infection of PER.C6 with a Large Variety of Influenza A and B Virus Strains

Figure 11:
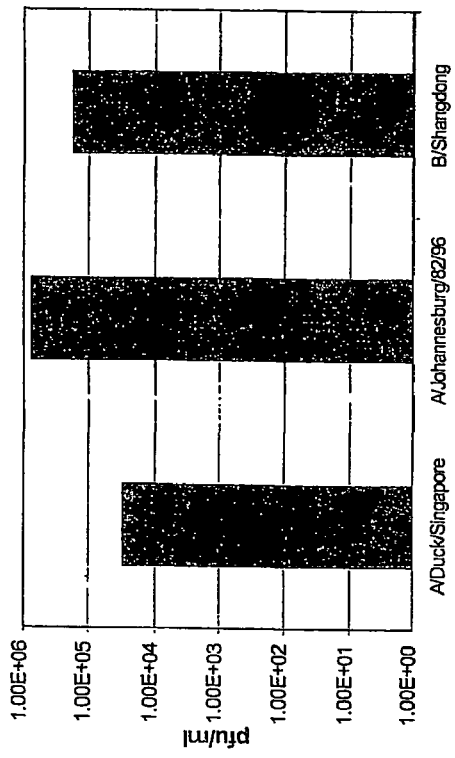
FIG. 11. (A) Different Influenza A and B strains tested on PER.C6 cells. (B) Infectivity titers of three depicted A-and B-type Influenza viruses derived from infected PER.C6 cells.

Static suspension cultures of PER.C6 cells that were grown in T25 flasks and/or in 6 well plates in ExCell 525 medium, were infected at a cell density of 10$^6$ cells/ml with 16 different strains of influenza viruses shown in FIG. 11A. These strains comprised several H3N2, H1N1, B type and avian strains. Infections were performed in the presence of 5 µg/ml of trypsin. The viruses were obtained from NIBSC (UK) as egg-passaged wild type or reassortant strains and are noted in. Infection was performed with a virus dilution recommended by the NIBSC in the product sheets that were delivered with the different strains. All viruses tested were capable of propagation on PER.C6 as visualized by immunofluorescence (data not shown) and titration of supernatant fluids in pfu assay (FIG. 11B).

These results show that even influenza strains (depicted by an asterisks), such as A/Johannesburg/33/94, B/Beijing/184/93 and A/Duck/Singapore-Q/F119-3/97, can replicate and be produced on the human PER.C6 cells.

Example 7

Generation of Herpes Simplex Type 1 (HSV-1) Virus, Herpes Simplex Type 2 (HSV-2) Virus and Measles Virus on PER.C6

It was tested whether viruses other than influenza virus and adenovirus, such as herpes simplex virus type 1 and 2 and measles virus could also replicate on PER.C6. Vaccines that are derived from these PER.C6-grown viruses and that induce neutralizing effects in humans for protection against wild type infections are generated from the PER.C6-grown virus batches. The strains that were obtained from ATCC and used for infection of PER.C6 cells are depicted in Table I.

Table I

Herpes simplex virus and Measles strains that were obtained from the ATCC and that were used for infection of PER.C6 cells.

| Virus | Strain | ATCC catnr. | Lotnr. | Passage history | Titer |
|---|---|---|---|---|---|
| Herpes Simplex Type 1 (HSV-1) | Macintyre | VR-539 | 1327850 | y.s./12, PR RabK/5, Mb/1, PrRabK/5, Vero/4, Vero (ATCC CC1-81)/1 | $10^{6.75}$ $TCID_{50}/200$ µl |
| Herpes Simplex Type 2 (HSV-2) | MS | VR-540 | 216463 | Sheep choroid plexus/?, HeLa/?, PrRabK/7, Vero (ATCC CC1-81) /3 | $10^{7.5}$ $TCID_{50}200$ µl |
| Measles | Edmonston | VR-24 | 215236 | HK/24, HuAm/40, MRC-5/1, MRC-5 (ATCC CCL-171) /1 | $10^4$ $TCID_{50}/ml$ |

Figure 12A:
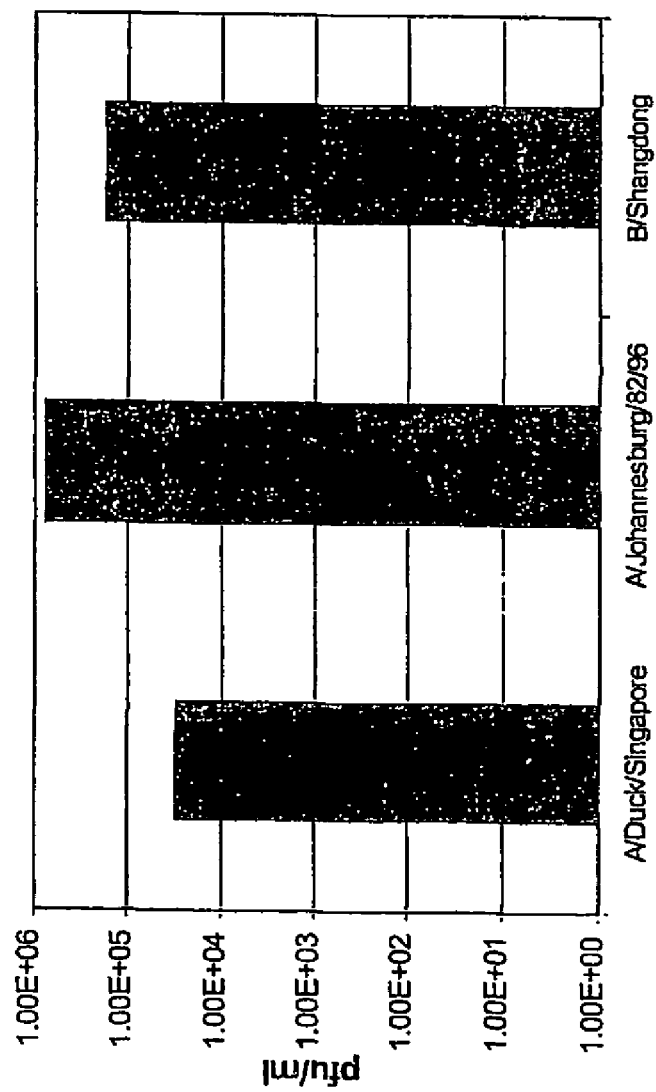
FIG. 12. Immunofluorescence of PER.C6 and Vero cells infected with viruses other than Influenza. (A) Positively staining cells upon infection with Measles virus. (B) Positively staining cells upon infection of Vero cells with HSV-1 virus. (C) Positively staining cells upon infection of Vero cells with HSV-2 virus. (D) Positively staining cells upon infection of PER.C6 cells with HSV-1 virus. (E) Positively staining cells upon infection of PER.C6 cells with HSV-2 virus.

To test whether HSV-1 and HSV-2 and measles viruses obtained from the ATCC could replicate and be produced on PER.C6, passage number 46 cells were seeded in labtek chambers, coated with poly-L-Lysine using methods known to persons skilled in the art, at $10^5$ cells/well. Monkey derived Vero cells (obtained from ATCC) were cultured at passage number 137 and were used as positive controls and seeded at a density of $2.5 \times 10^4$ cells/well. At dayO, when wells with PER.C6 cells were 60% and Vero cells 80% confluent, cells were infected with different moi's ($10^{-3}$, $10^{-2}$, $10^{-1}$ and 1 $TCID_{50}$ per cell). At daily intervals upon infection, cells were fixed and assayed in immunofluorescence using FITC-conjugated type specific monoclonal antibodies using a kit (Imagen Herpes Simplex Virus (HSV) Type 1 and 2, (Dako) and FITC-conjugated antibodies against the HA and matrix protein of measles virus (measles IFA kit, Light. diagnostics), following the procedures suggested by the manufacturer. The antisera are directed against HSV-1 and -2 and Measles virus antigens. The results summarized in FIG. 12 show that PER.C6 is permissive for HSV-1, HSV-2 and Measles virus infections. Furthermore, the kinetics suggest that these viruses replicate on PER.C6 in an moi-dependent manner.

Figure 13A:
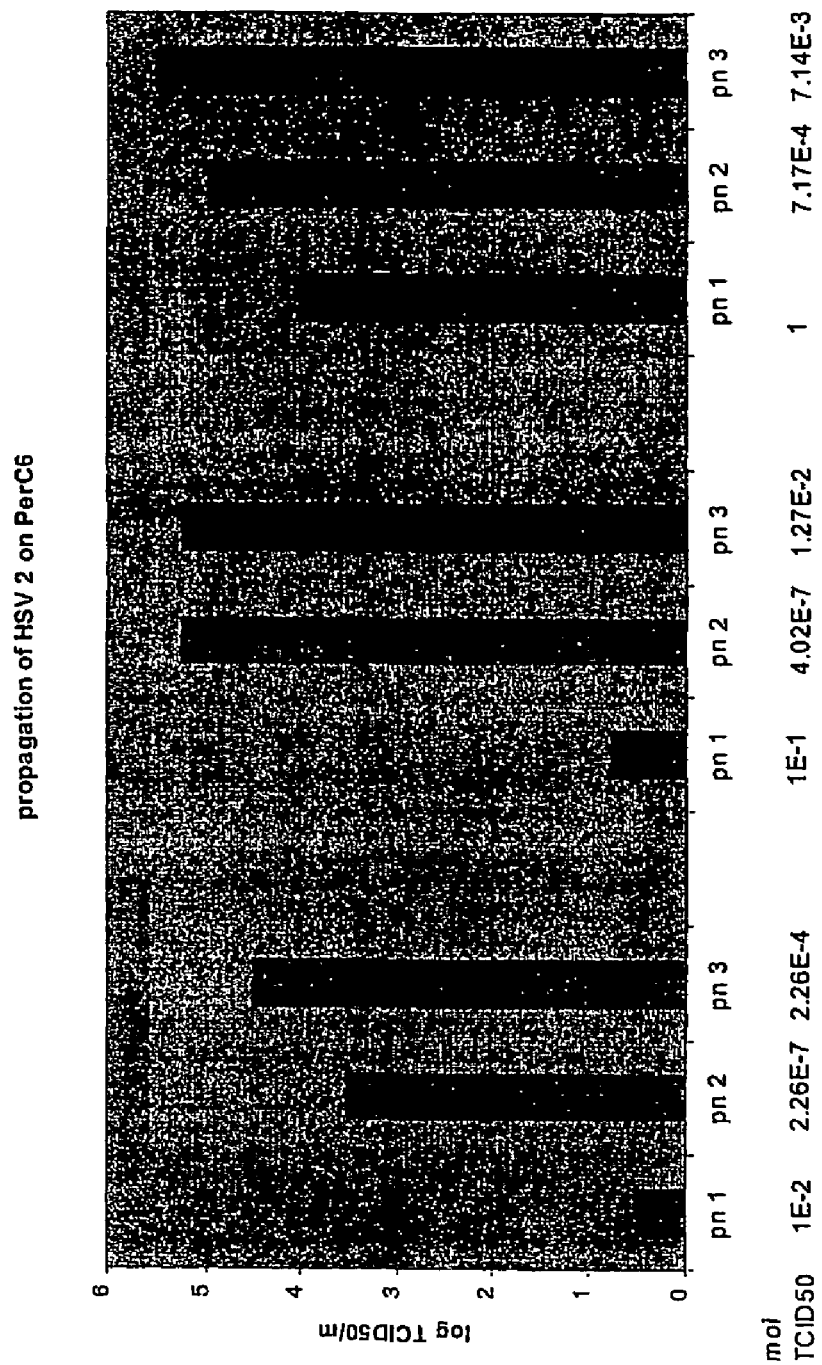
FIG. 13. Infectivity titers determined after propagation of Measles virus (A), HSV-1 (B) and HSV-2 (C) virus on PER.C6 cells.
Figure 13B:
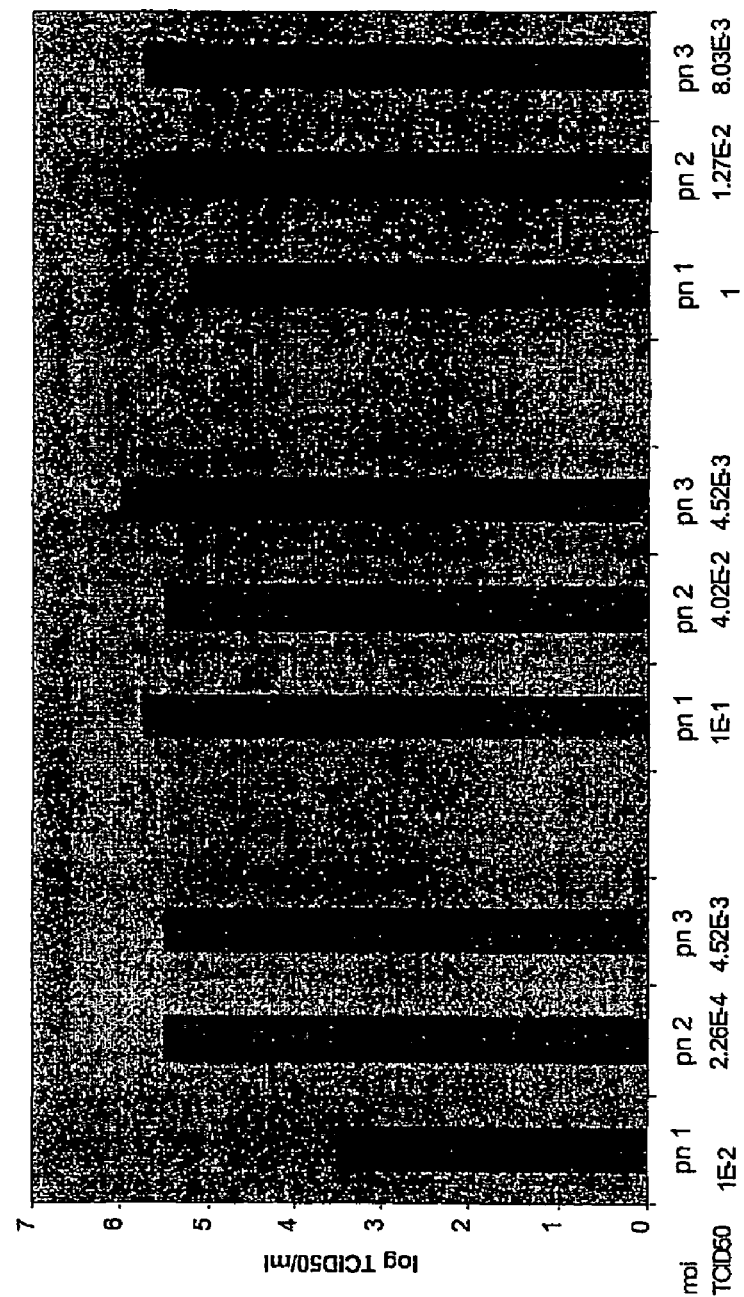
Figure 13C:
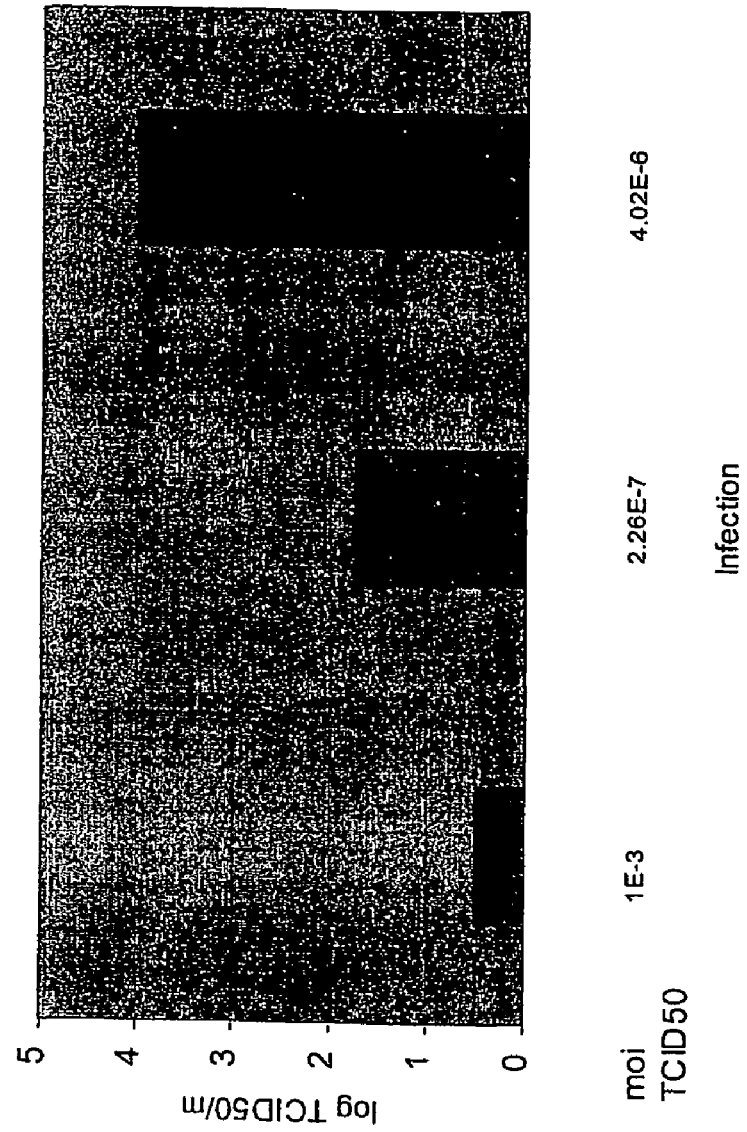

Next, it was investigated whether HSV-1, HSV-2 and measles virus could be propagated on PER.C6. To this end, cells were infected with moi of 0.01, 0.1 and 1 $TCID_{50}$/cell for HSV-1 (FIG. 13B) and HSV-2 (FIG. 13A) and an moi of 0.001 $TCID_{50}$/cell for measles virus (FIG. 13C) (passage number 1). At the occurrence of almost complete cpe, cells and supernatants were harvested, quickly frozen in liquid $N_2$, and thawed. After this, clarified supernatants were passaged blindly using approximately 100 µl, to PER.C6 (this is passage number 2). After reaching almost complete CPE again, a third passage (passage number 3) was performed in a similar manner. The moi's of the passage number 2 and 3 were determined in retrospect by $TCID_{50}$ assays. The results of these experiments show that HSV-1 and HSV-2 and measles viruses can be replicated on PER.C6 and that replication and propagation can even occur when moi's as low as $10^{-7}$ are used.

Example 8

Screening of Rotavirus for Replication on PER.C6

Figure 14A:
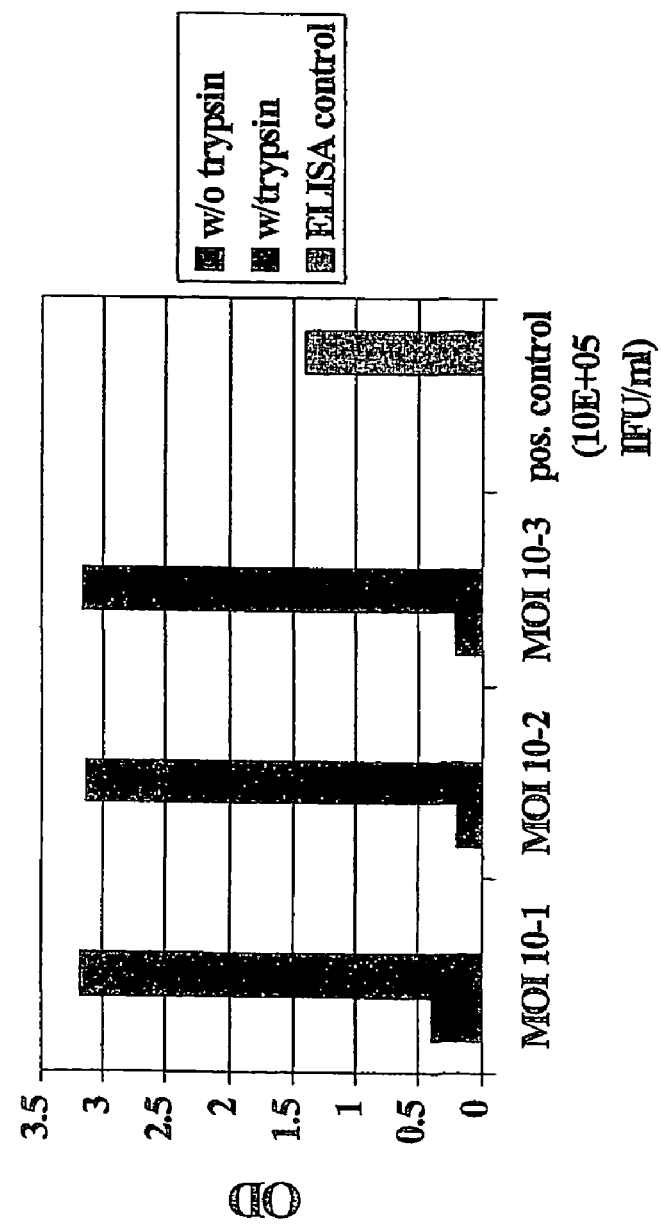
FIG. 14. Replication of Rotavirus after infection of PER.C6 (A) and Vero (B) cells with different moi's as measured by ELISA in crude supernatants.
Figure 14B:
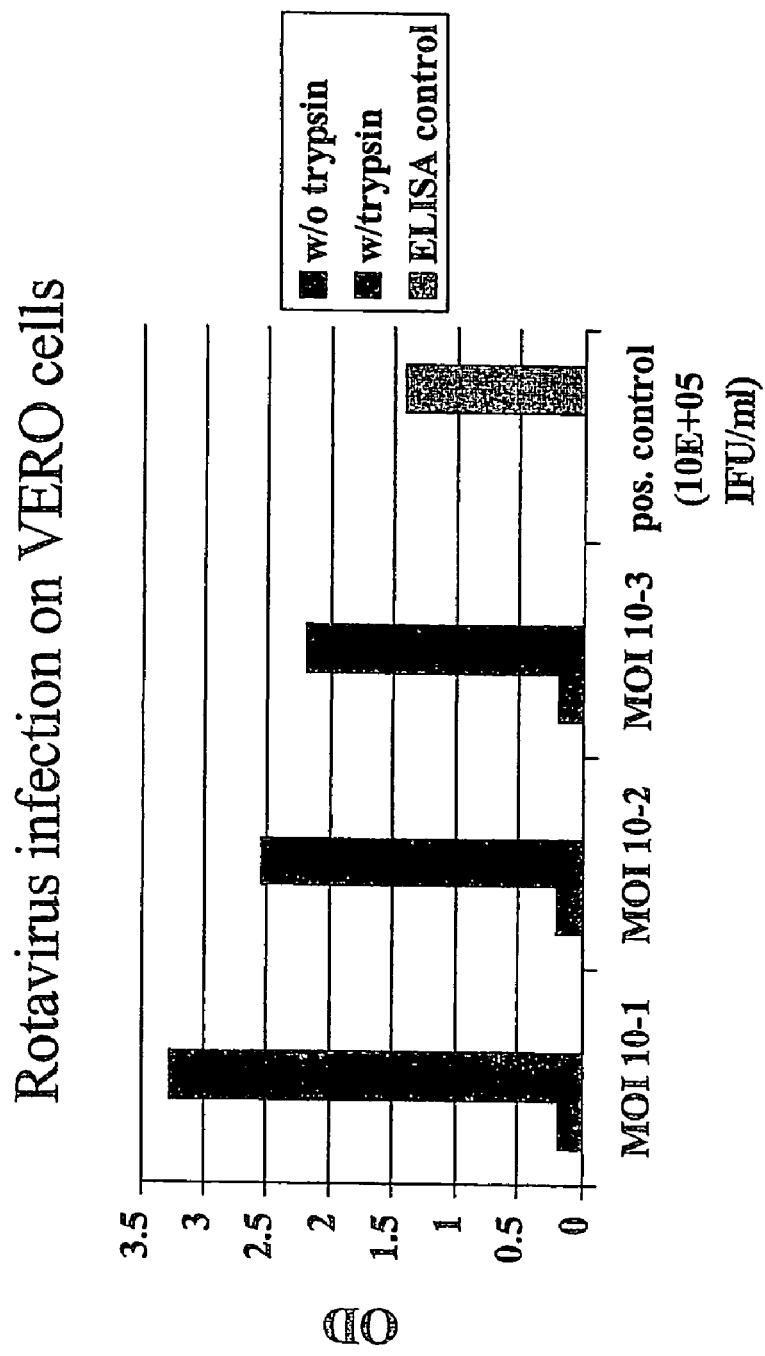

To test whether PER.C6 could also support the replication of a rotavirus, PER.C6 cells were infected with a Rhesus rotavirus (MMU 18006;ATCC#VR-954; strain S:USA:79:2; lot#2181153). PER.C6 cells (passage number 41) were cultured at a density of $1 \times 10^5$ per ml and monkey-derived Vero cells (obtained from ATCC, passage number 139) were cultured at a density of $2.5 \times 10^4$ per ml, and subsequently seeded in Labtek chambers, that had been pre-coated with poly-L-Lysine using methods known to persons skilled in the art. Cells were infected with an moi of 1 $TCID_{50}$/cell of Rhesus rotavirus in the presence and absence of 2 µg/ml of trypsin-EDTA. After 90 min of infections, cells were washed with ExCell 525 medium and further incubated at 37° C. at 10% $CO_2$ in a humidified atmosphere. On 5 consecutive days following infection, samples of supernatants were harvested, clarified from cells and cell debris by centrifugation at 2000 rpm in a table top centrifuge and analyzed in an ELISA specific for rotavirus (IDEIA Rotavirus, Dako). The results depicted in FIG. 14 clearly show that Rhesus rotavirus replicates on PER.C6.

Example 9

Inhibition of Herpes Virus Propogation of PER.C6 by a Purine Nucleoside Analogue Acyclovir (2-amino-1,9-dihydro-9-[(2-hydroethoxy)methyl]-6H-purin-6-one), is a synthetic purine analogue with in vivo and in vitro inhibitory activity against HSV-1, HSV-2 and against Varicella Zoster virus (VZV). The activity in vitro of acyclovir is the highest against HSV-1, followed by decreasing activities against HSV-2 and VZV. The mechanism of antiviral activity of this compound, which is highly selective, is based on its affinity for the enzyme thymidine kinase (TK) encoded by HSV and VZV. Acyclovir is converted by TK in acyclovir monophosphate, a nucleoside analogue that is further converted into diphosphate by cellular guanylate kinase and into triphosphate by a number of cellular enzymes. Acyclovir triphosphate stops the replication of herpes virus DNA in in vitro infected cell cultures by 1) inhibition of viral DNA polymerase, 2) chain termination of the viral DNA and 3) inactivation of the viral DNA polymerase. The differential sensitivity of HSV-1, -2 and VZV is related to differences in phosphorylation efficiency by the viral TK's (De Clercq 2001).

To test the feasibility of PER.C6 for antiviral drug screening, the acyclovir/HSV system was used. A $TCID_{50}$ titration of both a HSV-1 as well as a HSV-2 stock virus produced on PER.C6 (titer 6000 $TCID_{50}$/ml) was performed in either the absence or in the presence of different concentrations of acyclovir. PER.C6 cells were seeded in a 96-wells tissue culture plate at a concentration of $1 \times 10^5$ cells/well, in normal culture medium, DMEM (Gibco) supplemented with heat inactivated FBS (origin US, Gibco) and 1 ml 4.9 M $MgCl_2$ (Sigma). The day after seeding, cells were pre-incubated with the appropriate acyclovir (20 mg/ml, Genthon) concentration being, 200, 20, 2, 0,2 and 0 µg/ml, diluted in normal culture medium, for 2 hours at 37° C. and 10% $CO_2$. A total of 20 wells were used per concentration. On a separate plate, series of tenfold dilutions of HSV-1 (VR-539 ATCC, 3rd passage on PER.C6) and HSV-2 (VR-540 ATCC, 3rd passage on PER.C6) were made in the appropriate medium, supplemented with the respective concentrations of acyclovir according to the scheme in Table II. After the pre-incubation with acyclovir, the medium was removed from the cells, and 100 µl of each of the viral dilutions with acyclovir present, were added to duplicate wells.

Table II. Titration scheme for testing acyclovir virustatic activity against HSV-1 and HSV-2 replicating on PER.C6.
Viral input HSV-1: HSV-1 titer: 5000 $TCID_{50}$/100 µl
Viral input HSV-2: HSV-2 titer: 5000 $TCID_{50}$/100 µl
$2 \times 10^5$ cells/well

| Virus dilution | Input virus ($TCID_{50}$) | Moi ($TCID_{50}$/cell) |
|---|---|---|
| $10^{-1}$ | 10000 | $5 \times 10^{-2}$ |
| $10^{-2}$ | 1000 | $5 \times 10^{-3}$ |
| $10^{-3}$ | 100 | $5 \times 10^{-4}$ |
| $10^{-4}$ | 10 | $5 \times 10^{-5}$ |
| $10^{-5}$ | 1 | $5 \times 10^{-6}$ |
| $10^{-6}$ | 0.1 | $5 \times 10^{-7}$ |
| $10^{-7}$ | 0.01 | $5 \times 10^{-8}$ |
| $10^{-8}$ | 0.001 | $5 \times 10^{-9}$ |

At day 6 post infection, CPE was scored in each of the wells and $TCID_{50}$ calculated according to the Karber method (1931), which is well known to persons skilled in the art. In addition, viable cells were scored with the MTS assay. Briefly, 25 µl of MTS substrate (Celltiter 96 Aqueous One Solution Cell Proliferation Assay, Promega) was added to the wells. Metabolic active cells will reduce the MTS tetrazolium into a collored formazan product. The substrate was left on the cells for 2 hours at 37° C. 10% $CO_2$, followed by reading the $OD_{490}$ in an ELISA reader.

Figure 15:
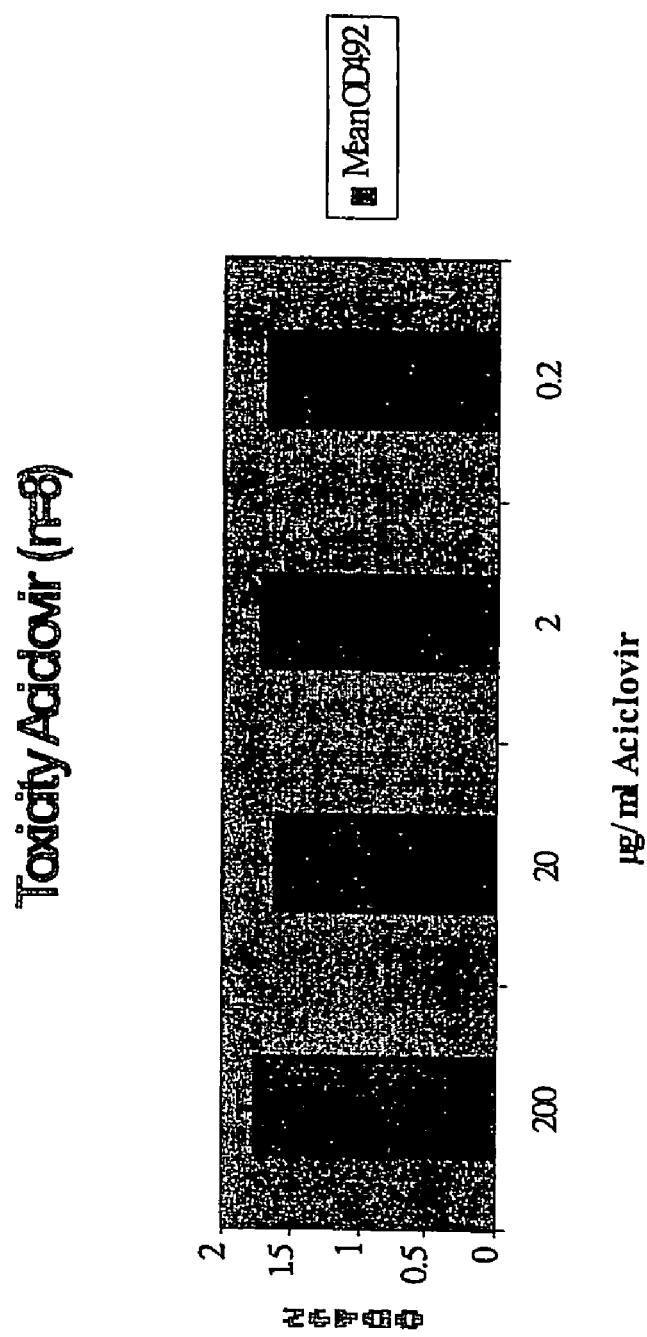
FIG. 15. Toxicity of acyclovir on PER.C6 as measured by MTS assay after 6 days of incubation of the cells in the presence of different dilution of the compound as indicated.
Figure 16:
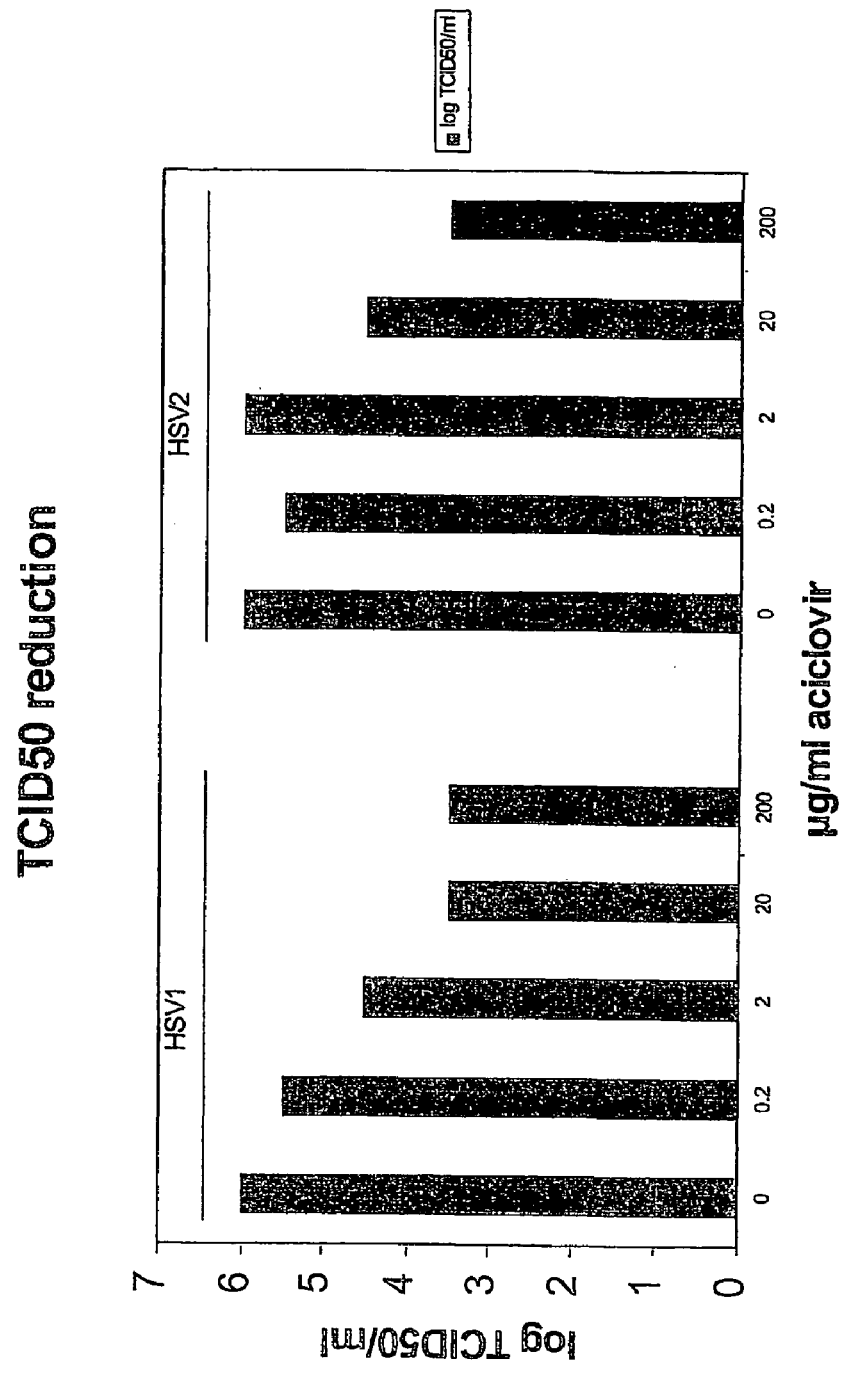
FIG. 16. Virustatic activity of acyclovir for Herpes Simplex Virus type 1 and type 2 (HSV-1 and HSV-2) using PER.C6 cells as a substrate for virus replication and $TCID_{50}$ calculations based on CPE score on day 6 post infection.
Figure 17A:
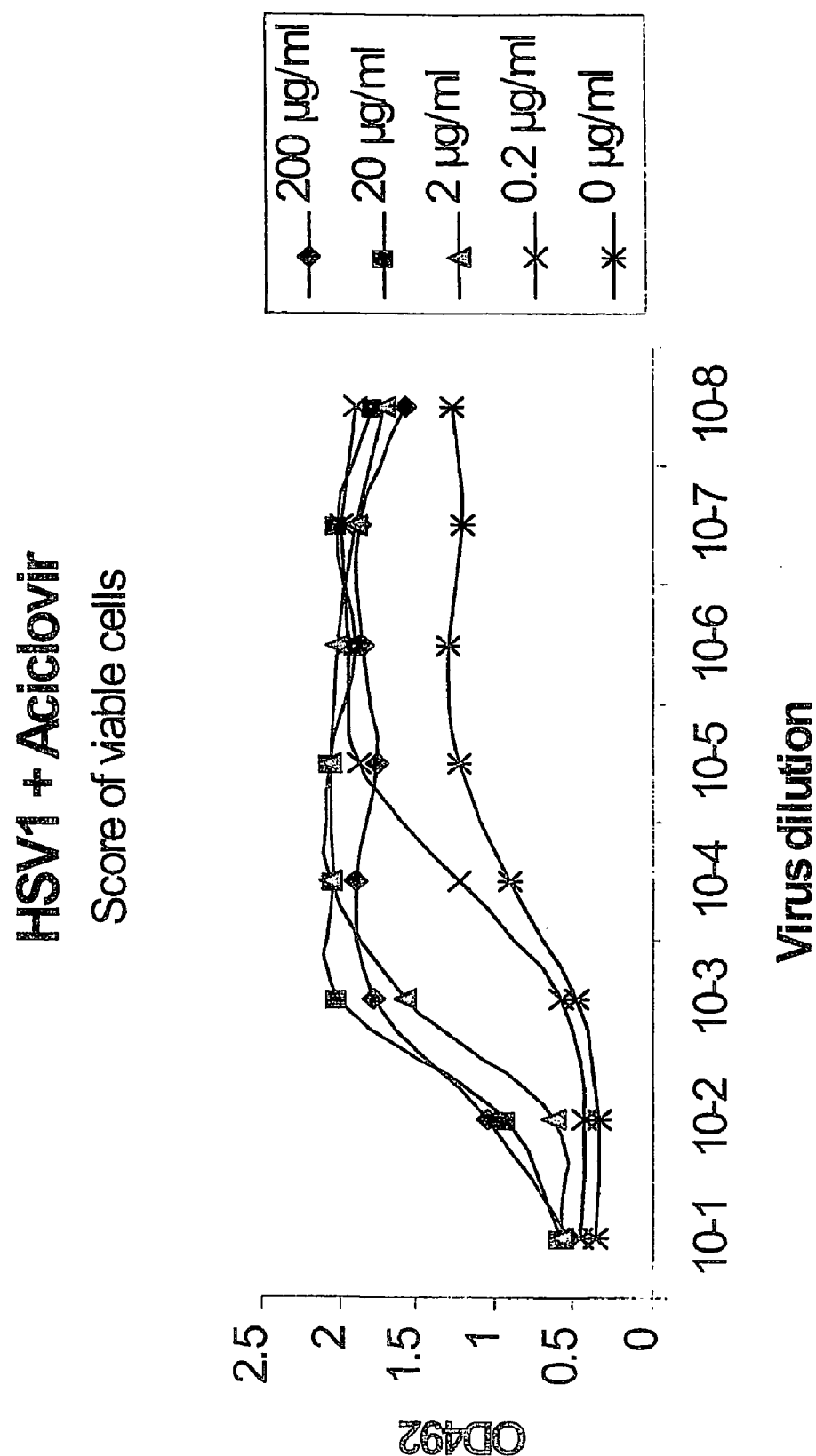
FIG. 17. Virustatic effect of acyclovir against (A) HSV-1 and (B) HSV-2 using infection of PER.C6 with different 10 fold serial dilutions of virus and viable cell scoring by MTS assay on day 6 post infection.
Figure 17B:
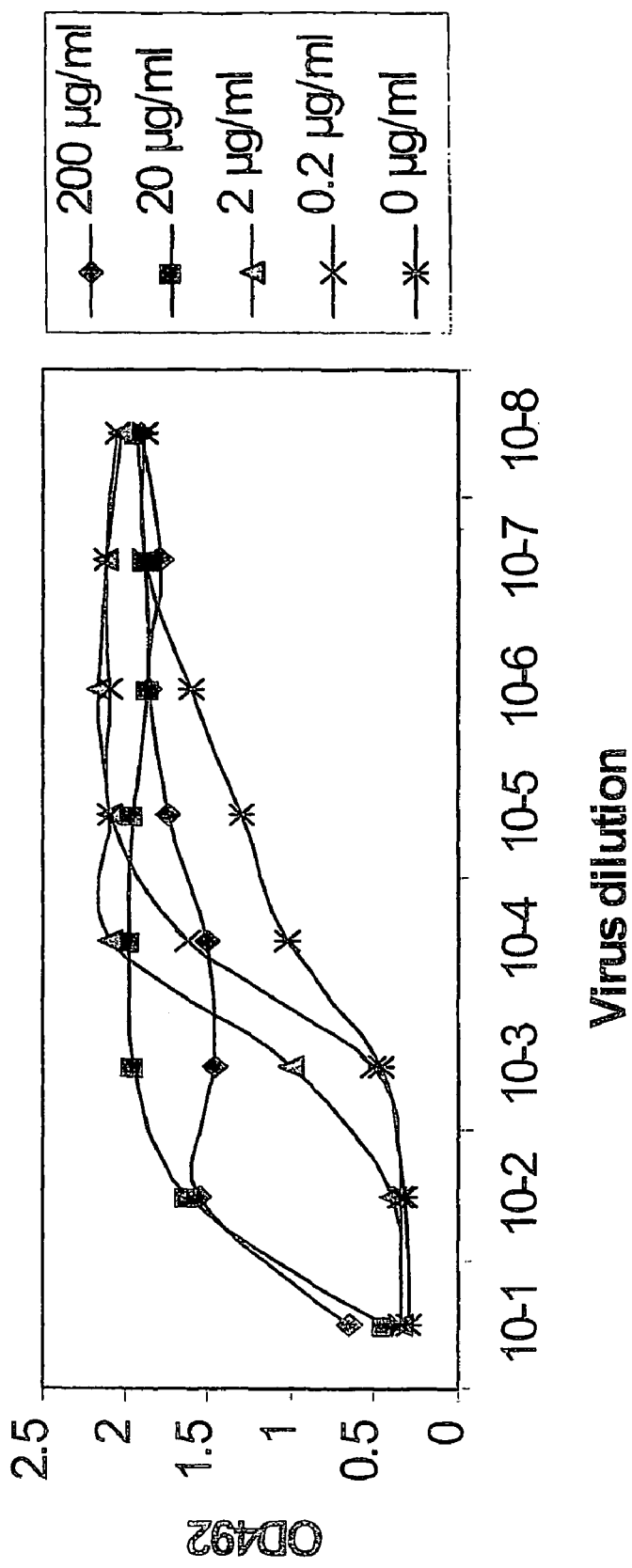

As shown in FIG. 15, no toxicity of acyclovir for uninfected PER.C6 cells was noticed, which is in agreement with its mechanism of action requiring phosphorylation by herpes virus TK. A clear virustatic effect of acyclovir was observed for both HSV-1 and HSV-2 when propagated on PER.C6 cells. For HSV-1, as compared to the control, an almost 1000 fold $TCID_{50}$ reduction was observed at a concentration of 20 µg/ml of acyclovir (FIG. 16 left panel). For HSV-2, a similar reduction of 1000 fold $TCDI_{50}$ required a higher amount of acyclovir (FIG. 16 right panel), which is in agreement with the differential sensitivity of HSV-2 for acyclovir. When scored for viable cells with MTS assay, which is well known to persons skilled in the art, comparable results were obtained (FIGS. 17A and B). Acyclovir was again found to be more effective at a lower dosage in preventing cell death caused by HSV-1 than by HSV-2, now by using PER.C6 cells.

REFERENCES

Alrabiah F A and Sacks (1996). New anti herpes virus agents. Their targets and therapeutic potential. Drugs 52: 17–32.

Bardsley-Elliot A and Plosker G L. (2000a) Nelfinavir: an update on its use in HIV infection. Drugs 59: 581–620.

Bardsley-Elliot A and Perry C M. (2000b) Nevirapine: a review of its use in the prevention and treatment of pediatric HIV infection. Pediatr Drugs 2: 373–407.

De Clercq E. (2001) Molecular targets for antiviral agents. J Pharmacol Exp Ther 297: 1–10.

Dwyer D E and Kesson A M (1997) Advances in antiviral therapy. Curr Opin Pediatr 9: 24–30.

Figgitt D P and Plosker G L. (2000) Saquinavir soft-gel capsule: an updated review of its use in the management of HIV infection. Drugs 60: 481–516.

Herrero-Uribe L, Mann G F, Zuckerman A J, Hockley D, Oxford J S. (1983) Replication of influenza A and B viruses in human diploid cells. J Gen Virol 64: 471–475.

Joly V, Moroni M, Concia E, Lazzarin A, Hirschel B, Jost J, Chiodo F, Bentwich Z, Love W C, Hawkins D A, Wilkins E G, Gatell A J, Vetter N, Greenwald C, Freimuth W W, de Cian W (2000). Delavirdine in combination with zidovudine in treatment of human immunodeficiency virus type 1-infected patients: evaluation of efficacy and emergence of viral resistance in a randomized, comparative phase III trial. The M/3331/0013B Study Group. Antimicrob Agents Chemother 44: 3155–3157.

Karber G. Beitrag zur kollektiven behandlung pharmakologischer reihenversuche. (1931) Exp. Pathol. Pharmakol 162: 480–483.

Keating M R (1999). Antiviral agents for non-human immunodeficiency virus infections. Mayo Clin Proc 74: 1266–1283.

Li X Q, Gorelik E, Atchison R W, Ovejera A and Ho M (1988). A new in vivo anti-viral assay using microencapsulated infected cell cultures. Antiviral Res 10: 179–192.

Murray M A and Babe L M (1999). Inhibitory effect of dibenzofuran and dibenzosuberol derivatives on rhinovirus replication in vitro; effective prevention of viral entry by dibenzosuberenone. Antiviral Res 44: 123–131.

Pastor-Anglada M, Felipe A and Casado F J (1998). Transport and mode of action of nucleoside derivatives used in chemical and antiviral therapies. Trends Pharmacol Sci 19: 424–30.

Polyak S J and Gerotto M (2000). The molecular basis for responsiveness to anti-viral therapy in hepatitis C. Forum (Genova) 10: 46–58.

Scott L J and Perry C M (2000). Delavirdine: a review of its use in HIV infection. Drugs 60: 1411–1444.

Sidwell R W and Smee D F (2000). In vitro and in vivo assay systems for study of influenza virus inhibitors. Antiviral Res 48: 1–16.

Todd S, Anderson C, Jolly D J and Craik C S (2000). HIV protease as a target for retrovirus vector-mediated gene therapy. Biochim Biophys Acta 1477: 168–188.

Ying C, De Clerq E and Neyts, J (2000). Lamivudine, adefovir and tenofovir exhibit long-lasting anti-hepatitis B virus activity in cell culture. J Viral Hepat 7: 79–83.

International patent application No. PCT/NL00/00862, int. filing date 24, Nov. 2000, "Production of vaccines" (PCT International Publication No. WO 01/38362).

What is claimed is:

1. A method for determining whether a compound interferes with a phase in the life cycle of a virus other than an adenovirus, said method comprising the steps of:
   (a) infecting a PER.C6™ human embryonic retina cell as deposited with the European Collection of Cell Cultures [ECACC] under accession number 96022940 with an essentially intact virus other than an adenovirus, said essentially intact virus comprising at least those elements of the virus sufficient for performing said phase in the virus' life cycle;
   (b) providing said PER.C6™ human embryonic retina cell with the compound; and
   (c) determining whether said phase in the virus' life cycle is interfered with by the compound,
wherein step (a) and (b) may be performed simultaneously, or in any order.

2. The method according to claim 1, wherein said cell further comprises a nucleic acid sequence encoding an adenovirus E2 protein.

3. The method according to claim 1, wherein determining whether the compound interferes with a phase in the life cycle of a virus comprises examining the virus' activity, the amount of the virus, the activity of a fragment of the virus, the amount of a fragment of the virus, or a mixture thereof.

4. A method for identifying a compound with antiviral activity, said method comprising the steps of:
   (a) infecting a PER.C6 ™ human embryonic retina cell as deposited with the European Collection of Cell Cultures [ECACC] under accession number 96022940 with an essentially intact virus other than an adenovirus, said virus able to perform a step in the life cycle of said virus;
   (b) providing said cell with a compound; and
   (c) determining whether said compound is able to influence said step in the life cycle of said virus, wherein step (a) and (b) may be performed simultaneously, or in any order.

5. The method according to claim 4, wherein said compound is part of a compound library.

6. The method according to claim 4, wherein the method is performed in a high-throughput setting.

7. The method according to claim 4, wherein said method further comprises the step of isolating said compound.

* * * * *